(12) United States Patent
Kishino et al.

(10) Patent No.: US 8,932,736 B2
(45) Date of Patent: Jan. 13, 2015

(54) ORGANIC COMPOUND AND ORGANIC LIGHT-EMITTING DEVICE

(75) Inventors: Kengo Kishino, Tokyo (JP); Yosuke Nishide, Kawasaki (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 331 days.

(21) Appl. No.: 13/578,682

(22) PCT Filed: Feb. 10, 2011

(86) PCT No.: PCT/JP2011/000758
§ 371 (c)(1),
(2), (4) Date: Aug. 13, 2012

(87) PCT Pub. No.: WO2011/102102
PCT Pub. Date: Aug. 25, 2011

(65) Prior Publication Data
US 2012/0313085 A1    Dec. 13, 2012

(30) Foreign Application Priority Data
Feb. 16, 2010  (JP) ................. 2010-031659

(51) Int. Cl.
| | |
|---|---|
| H01L 51/54 | (2006.01) |
| C07C 13/62 | (2006.01) |
| H01L 27/32 | (2006.01) |
| C07D 209/86 | (2006.01) |
| C07C 22/08 | (2006.01) |
| C07C 25/22 | (2006.01) |
| C07C 43/275 | (2006.01) |
| C07C 211/61 | (2006.01) |
| C09K 11/06 | (2006.01) |
| H01L 51/00 | (2006.01) |
| H05B 33/14 | (2006.01) |

(52) U.S. Cl.
CPC .............. *C07D 209/86* (2013.01); *C07C 13/62* (2013.01); *C07C 22/08* (2013.01); *C07C 25/22* (2013.01); *C07C 43/275* (2013.01); *C07C 211/61* (2013.01); *C09K 11/06* (2013.01); *H01L 51/0056* (2013.01); *H05B 33/14* (2013.01); *C07C 2103/40* (2013.01); *C07C 2103/54* (2013.01); *C09K 2211/1011* (2013.01); *Y10S 428/917* (2013.01)
USPC ............. 428/690; 428/917; 585/27; 313/504; 313/506

(58) Field of Classification Search
None
See application file for complete search history.

(56) References Cited

U.S. PATENT DOCUMENTS 7,183,010 B2    2/2007  Jarikov
2002/0168544 A1*  11/2002  Fukuoka et al. .............. 428/690

FOREIGN PATENT DOCUMENTS

| JP | 2008-290999 A | 12/2008 |
| JP | 2009-221180 A | 10/2009 |
| JP | 2010-143879 A | 7/2010 |

OTHER PUBLICATIONS

Goverdhan Mehta and Srirama Sarma, "A rapid, two step construction of novel C48H24 and C54H24 polycyclic aromatic hydrocarbons represented on the C60-fullerene surface via a threefold intramolecular Heck coupling reaction", Tetrahedron Letters 43 (2002) 6557-6560.

*Primary Examiner* — Dawn L. Garrett
(74) *Attorney, Agent, or Firm* — Canon U.S.A. Inc., IP Division

(57) ABSTRACT

A novel organic compound suitable for blue light emission and an organic light-emitting device containing the novel organic compound are provided. An organic compound represented by the following general formula (1) wherein $R_1$ to $R_{18}$ independently denote a hydrogen atom, a halogen atom, a substituted or unsubstituted alkyl group, a substituted or unsubstituted alkoxy group, a substituted or unsubstituted amino group, a substituted or unsubstituted aryl group, or a substituted or unsubstituted heterocyclic group.

[Chem. 2]
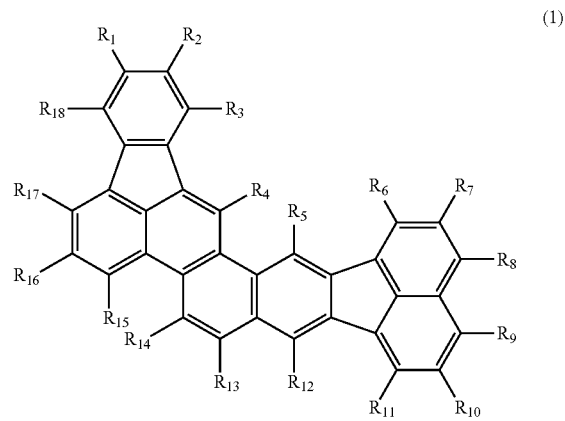
(1)
8 Claims, 1 Drawing Sheet

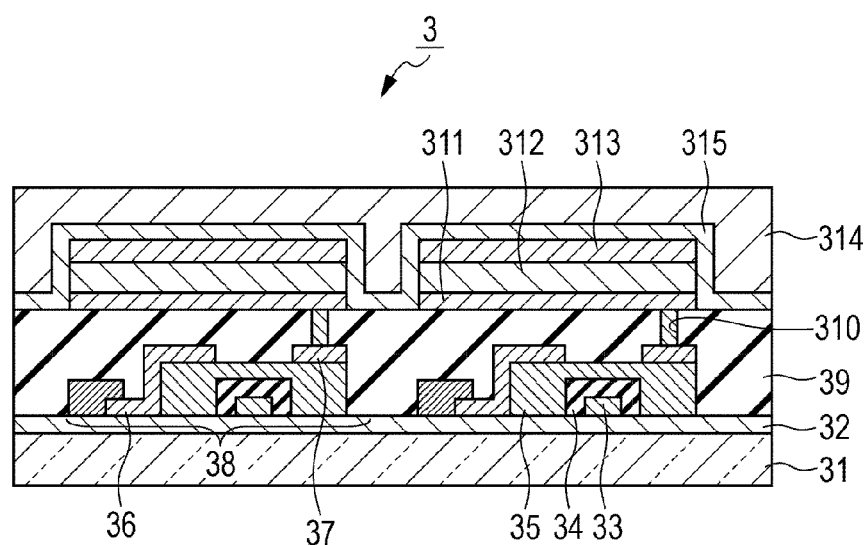

ORGANIC COMPOUND AND ORGANIC LIGHT-EMITTING DEVICE

TECHNICAL FIELD

The present invention relates to a novel organic compound and an organic light-emitting device containing the novel organic compound.

BACKGROUND ART

Organic light-emitting devices include an anode, a cathode, and an organic compound layer between the anode and the cathode. Positive holes (holes) and electrons from the electrodes recombine to form excitons in the organic compound layer. The organic light-emitting devices emit light while the excitons return to their ground state. Organic light-emitting devices are also referred to as organic electroluminescent (EL) devices.

Recent years have seen significant advances in organic light-emitting devices, resulting in light-emitting devices having a low driving voltage, various emission wavelengths, a high-speed responsivity, a low profile, and a light weight.

Novel light-emitting compounds are being actively developed. This is because the novel light-emitting compounds are important for the development of high-performance organic light-emitting devices.

For example, as an exemplary organic compound, PTL 1 discloses a compound 1 (indeno[1,2,3-hi]chrysene) described below.

[Chem. 1]

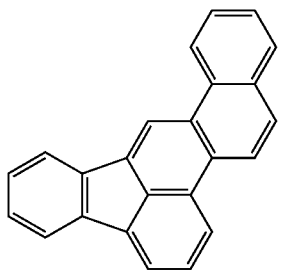

Compound 1

CITATION LIST

Patent Literature

PTL 1: U.S. Pat. No. 7,183,010

SUMMARY OF INVENTION

Technical Problem

This compound has a quantum yield as low as 0.37 and is therefore not suitable for use in organic light-emitting devices.

The present invention provides a novel organic compound the basic skeleton of which alone can emit light in a blue region.

Solution to Problem

The present invention provides an organic compound represented by the following general formula (1):

[Chem. 2]

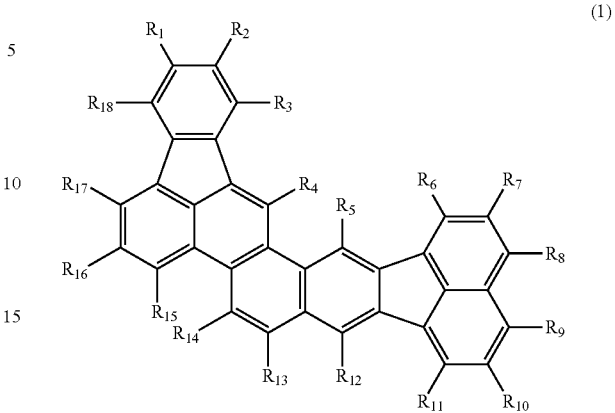

(1)

wherein $R_1$ to $R_{18}$ independently denote a hydrogen atom, a halogen atom, a substituted or unsubstituted alkyl group, a substituted or unsubstituted alkoxy group, a substituted or unsubstituted amino group, a substituted or unsubstituted aryl group, or a substituted or unsubstituted heterocyclic group.

Advantageous Effects of Invention

The present invention can provide a novel organic compound the basic skeleton of which alone has a band gap suitable for a blue region. The present invention can also provide a novel organic compound that can emit green or red light as well as blue light by the introduction of a substituent into the basic skeleton. The present invention can also provide an organic light-emitting device containing the novel organic compound.

BRIEF DESCRIPTION OF DRAWINGS

FIG. 1 is a schematic cross-sectional view of an organic light-emitting device and a switching device, which is connected to the organic light-emitting device.

DESCRIPTION OF EMBODIMENTS

An organic compound according to an embodiment of the present invention will be described below.

A novel organic compound according to an embodiment of the present invention has a structure represented by the following general formula (1):

[Chem. 3]

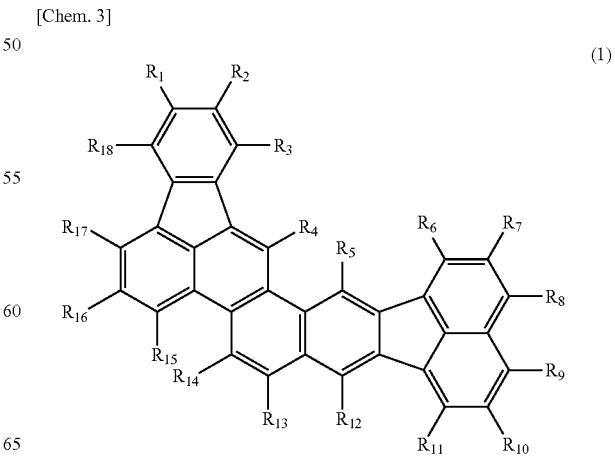

(1)

wherein $R_1$ to $R_{18}$ independently denote a hydrogen atom, a halogen atom, a substituted or unsubstituted alkyl group, a substituted or unsubstituted alkoxy group, a substituted or unsubstituted amino group, a substituted or unsubstituted aryl group, or a substituted or unsubstituted heterocyclic group.

In the structure represented by the general formula (1), a fused ring structure without $R_1$ to $R_{18}$ is referred to as the basic skeleton.

These alkyl, alkoxy, amino, aryl, and heterocyclic groups can provide green or red light emission, as well as blue light emission.

Examples of the alkyl group of the substituted or unsubstituted alkyl group include, but are not limited to, a methyl group, an ethyl group, a normal propyl group, an isopropyl group, a normal butyl group, a tertiary butyl group, a secondary butyl group, an octyl group, a 1-adamantyl group, and a 2-adamantyl group.

Examples of the alkoxy group of the substituted or unsubstituted alkoxy group include, but are not limited to, a methoxy group, an ethoxy group, a propoxy group, a 2-ethyloctyloxy group, a phenoxy group, a 4-tertiary butylphenoxy group, a benzyloxy group, and a thienyloxy group.

Examples of the amino group of the substituted or unsubstituted amino group include, but are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianysolylamino group, an N-mesityl-N-phenylamino group, an N,N-dimesitylamino group, an N-phenyl-N-(4-tertiary butylphenyl)amino group, and an N-phenyl-N-(4-trifluoromethylphenyl)amino group.

In the formula (1), examples of the aryl group of the substituted or unsubstituted aryl group include, but are not limited to, a phenyl group, a naphthyl group, an indenyl group, a biphenyl group, a terphenyl group, and a fluorenyl group. A phenyl group is desirable.

In the formula (1), examples of the heterocyclic group of the substituted or unsubstituted heterocyclic group include, but are not limited to, a pyridyl group, an oxazolyl group, an oxadiazolyl group, a thiazolyl group, a thiadiazolyl group, a carbazolyl group, an acridinyl group, and a phenanthryl group.

In the formula (1), examples of substituents, that is, substituents on the alkyl group, the alkoxy group, the amino group, the aryl group, and the heterocyclic group include, but are not limited to, alkyl groups, such as a methyl group, an ethyl group, a propyl group, and a tertiary butyl group; aralkyl groups, such as a benzyl group; aryl groups, such as a phenyl group and a biphenyl group; heterocyclic groups, such as a pyridyl group and a pyrrolyl group; amino groups, such as a dimethylamino group, a diethylamino group, a dibenzylamino group, a diphenylamino group, and a ditolylamino group; alkoxy groups, such as a methoxy group, an ethoxy group, a propoxy group, and a phenoxy group; a cyano group; and halogen atoms, such as fluorine, chlorine, bromine, and iodine. Alkyl groups, particularly a methyl group and a tertiary butyl group, are desirable.

It is known that a substituent is introduced into a basic skeleton to secure a desired emission wavelength. This substituent, however, may impair the stability of the compound. Thus, the present inventors have focused on the basic skeleton. More specifically, the present inventors have tried to provide a compound the basic skeleton molecules of which alone have a desired emission wavelength range (that is, a blue region; more specifically, the peak wavelength or the maximum emission wavelength of the emission spectrum of 430 nm or more and 480 nm or less).

Comparison between Indeno[1,2,3-hi]chrysene Derivative and Acenaphtho[1,2-b]indeno[1,2,3-hi]chrysene Derivative Indeno[1,2,3-hi]chrysene and acenaphtho[1,2-b]indeno[1,2,3-hi]chrysene have the following structural formulae.

[Chem. 4]

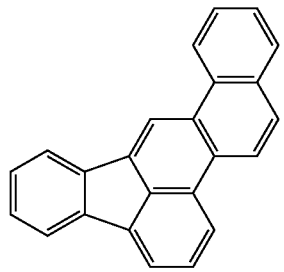

Indeno[1,2,3-hi]chrysene

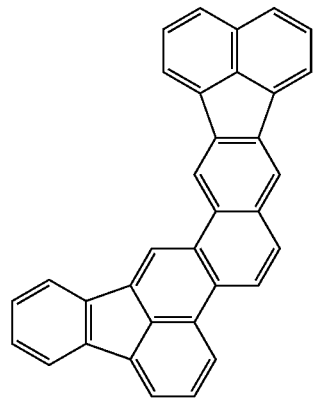

Acenaptho[1,2-b]indeno[1,2,3-hi]chrysene

Table 1 shows the comparison in light-emitting properties between an organic compound according to an embodiment of the present invention and indeno[1,2,3-hi]chrysene.

TABLE 1

[Chem. 5]

| | Structure | Maximum emission wavelength (nm) | Quantum yield |
|---|---|---|---|
| A | 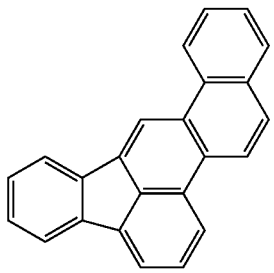 [SMILES: c1ccc2c(c1)-c1cccc3c1c-2cc1c2ccccc2ccc31] | 420 | 0.37 |

TABLE 1-continued

[Chem. 5]

| Structure | Maximum emission wavelength (nm) | Quantum yield |
|---|---|---|
| B (structure shown) | 430 | 0.76 |

Although the emission wavelength of an organic compound A (indeno[1,2,3-hi]chrysene) in Table 1 can be controlled by the addition of a substituent, the organic compound A has a low quantum yield. It is therefore difficult to manufacture a high-efficiency (more specifically, an external quantum efficiency of 4% or more) organic light-emitting device. In order to manufacture a high-efficiency organic light-emitting device, the light-emitting material should have a quantum yield of at least 0.50.

In contrast, the organic compound B (acenaphtho[1,2-b]indeno[1,2,3-hi]chrysene) advantageously has a quantum yield of at least 0.50 (0.76).

An organic compound according to an embodiment of the present invention has two five-membered ring structures in its basic skeleton and has a lower highest occupied molecular orbital (HOMO) energy level, that is, a low oxidation potential. Thus, an organic compound according to an embodiment of the present invention is resistant to oxidation.

An organic compound according to an embodiment of the present invention does not have a heteroatom, such as a nitrogen atom, in its basic skeleton. This also contributes to lower oxidation potential, that is, high resistance of the organic compound to oxidation.

The basic skeleton of an organic compound according to an embodiment of the present invention has a lower HOMO energy level, that is, a lower LUMO energy level.

An organic compound according to an embodiment of the present invention can be a blue-light-emitting material, a green-light-emitting material, or a red-light-emitting material by the introduction of a substituent for increasing the emission wavelength into the basic skeleton. These long-wavelength materials have the same basic skeleton as an organic compound according to an embodiment of the present invention and are therefore resistant to oxidation even when the materials have the substituent. Examples of the substituent for increasing the emission wavelength to a green region include, but are not limited to, triarylamine and anthracene.

An organic compound according to an embodiment of the present invention can be used as a guest material or a host material for a light-emitting layer. An organic compound according to an embodiment of the present invention may be used in any layer other than the light-emitting layer, that is, a hole-injection layer, a hole-transport layer, a hole-exciton-blocking layer, an electron-transport layer, or an electron-injection layer. The luminescent color of the organic light-emitting device is not limited to blue and may be green, red, white, or a neutral color. When an organic compound according to an embodiment of the present invention is used for white light emission, one light-emitting layer may contain a plurality of light-emitting materials different from the organic compound. Alternatively, a plurality of light-emitting layers containing a light-emitting material different from an organic compound according to an embodiment of the present invention may be stacked. The light-emitting material different from an organic compound according to an embodiment of the present invention may be a phosphorescent material or a fluorescent material.

In the case that an organic compound according to an embodiment of the present invention is used as a guest material for the light-emitting layer, the light-emitting layer contains the guest material and a host material. In particular, it is desirable that an organic compound according to one embodiment of the present invention be used as a guest material for a blue-light-emitting device. Among the compounds constituting the light-emitting layer, the host material serves as a main component, and the guest material is a compound having a lower weight ratio than the host material.

When an organic compound according to an embodiment of the present invention is used as the guest material for the light-emitting layer, it is desirable that the host material be a material having a higher LUMO level than the organic compound, that is, a material having an energy level closer to the vacuum level. This is because an organic compound according to an embodiment of the present invention has a low LUMO level and can accept electrons smoothly from the host material in the light-emitting layer.

An organic compound according to an embodiment of the present invention may be used as a host material, as well as a guest material. Furthermore, an organic compound according to an embodiment of the present invention may be used as a host material for a blue-light-emitting layer, a green-light-emitting layer, or a red-light-emitting layer.

Organic Compounds According to Embodiments of the Present Invention

Organic compounds according to embodiments of the present invention can be classified into the following A to D groups.

[Chem. 6]

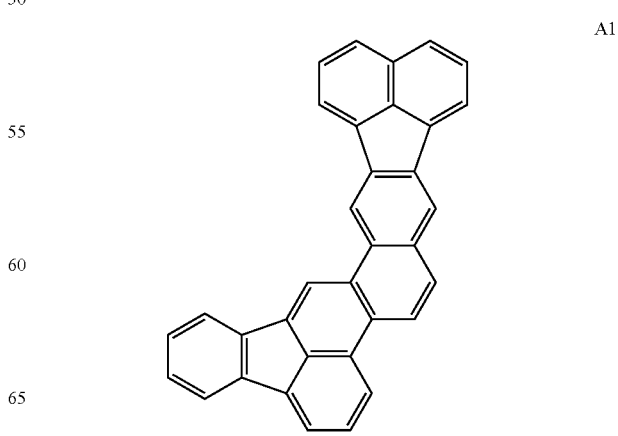

A1

A2
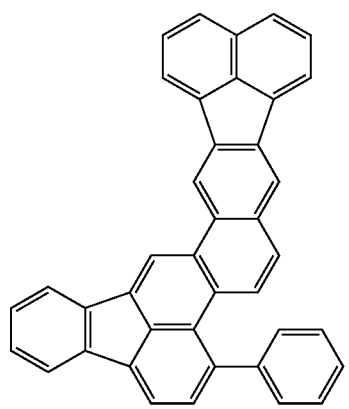
A3
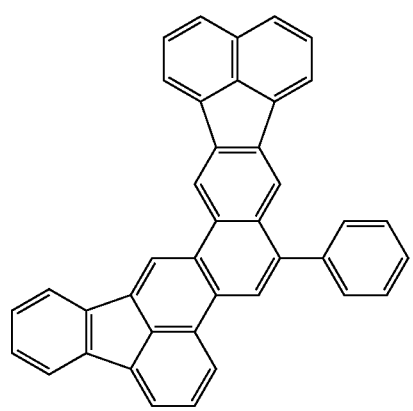
A4
A5
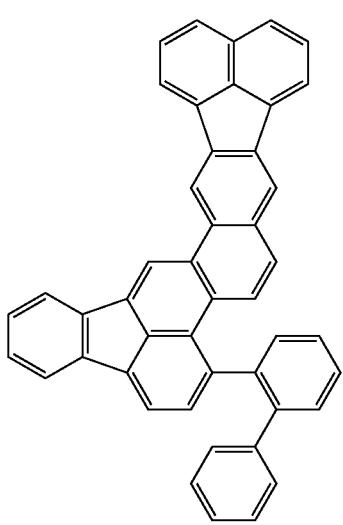
A6
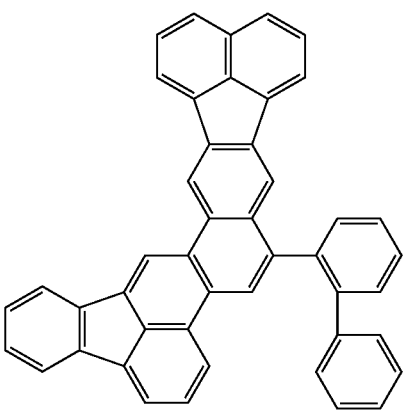
A7
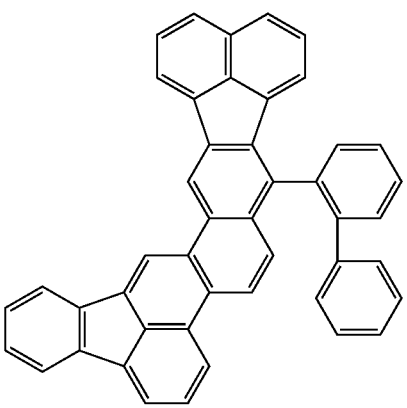

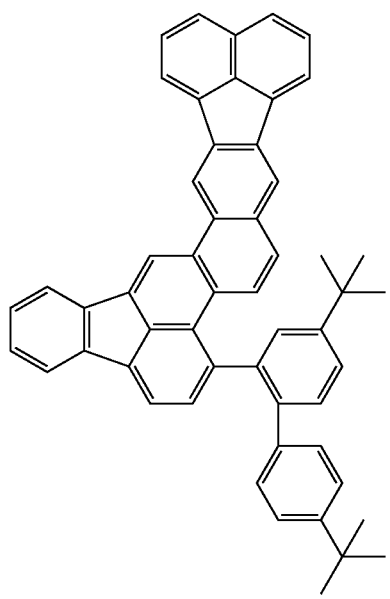 A8
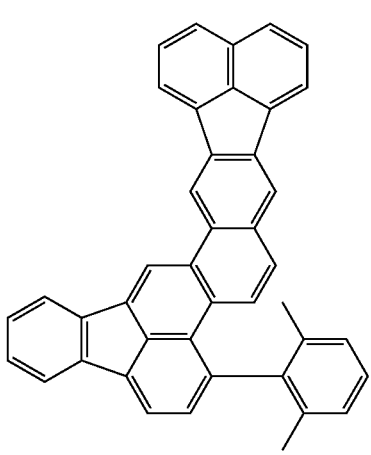 A11
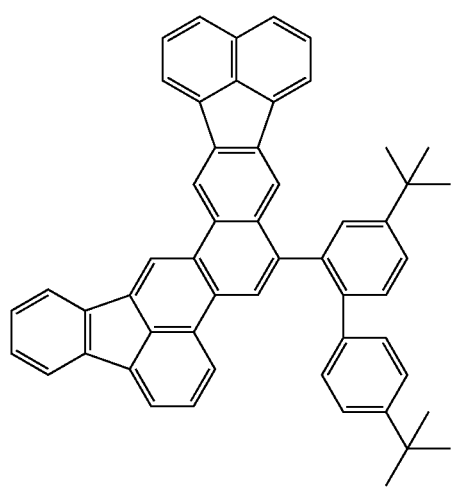 A9
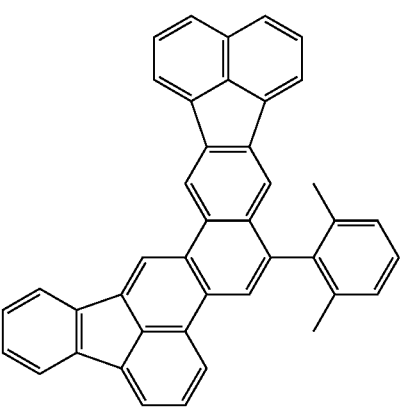 A12
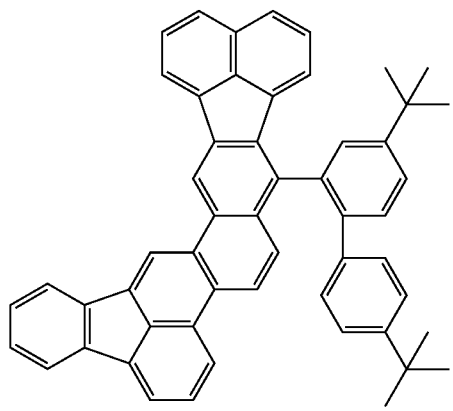 A10
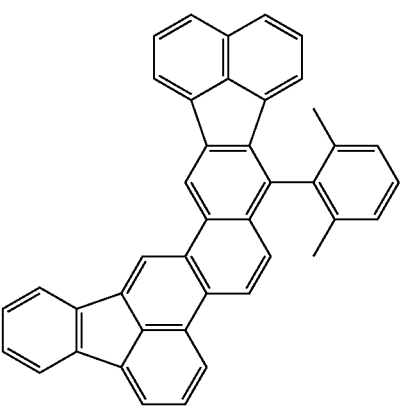 A13

[Chem. 7]
A14
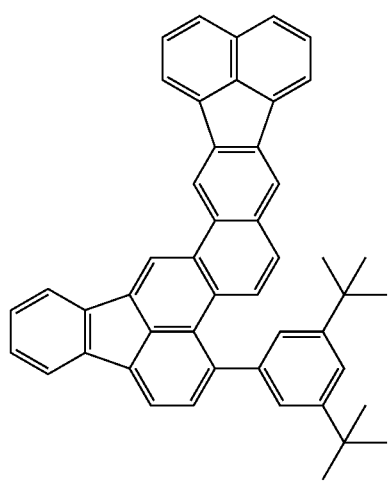
A15
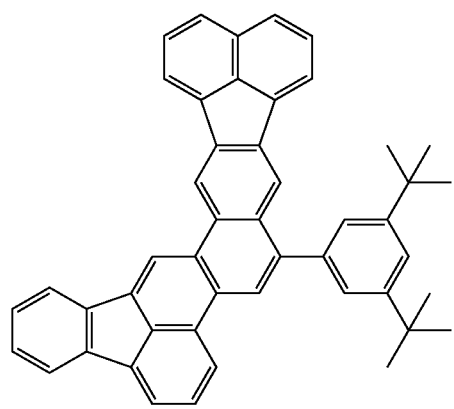
A16
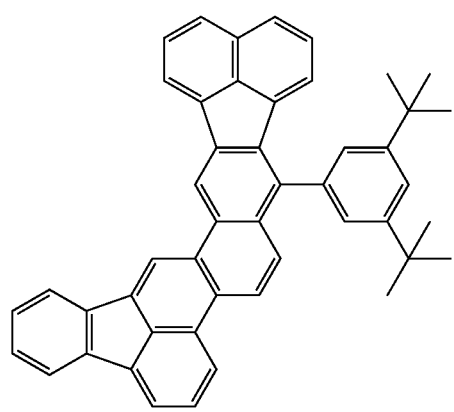
A17
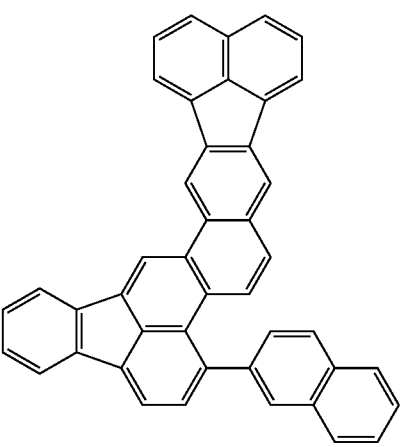
A18
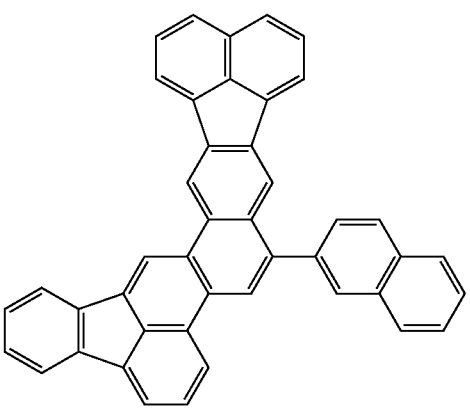
A19
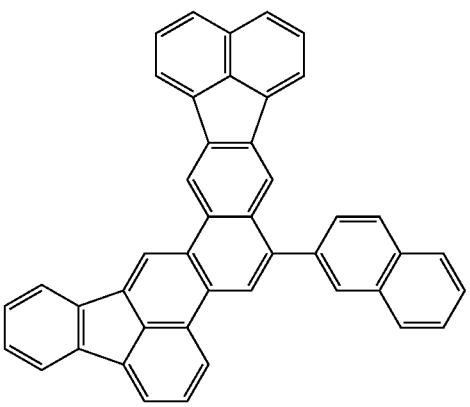

A20
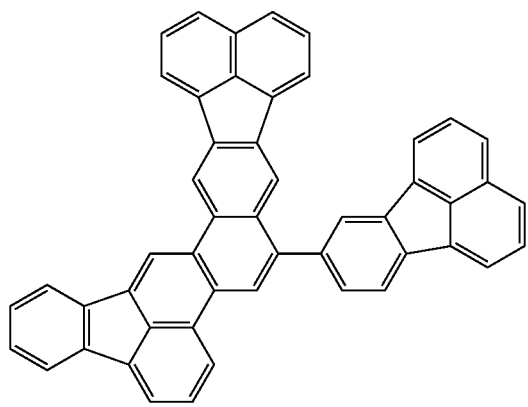
A23
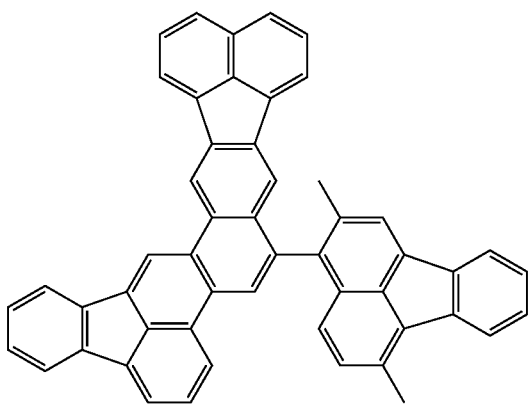
A21
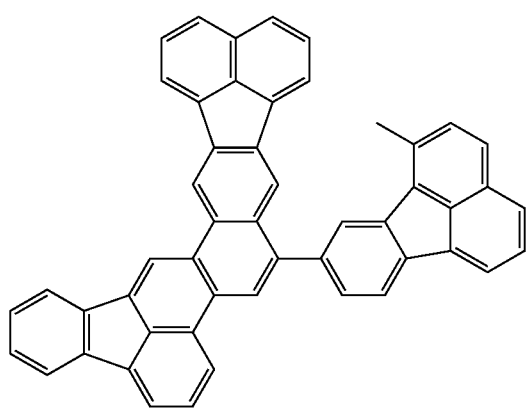
A24
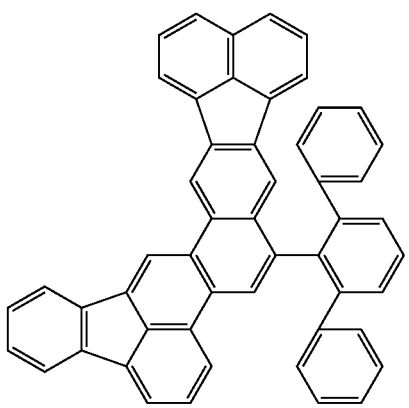
A22
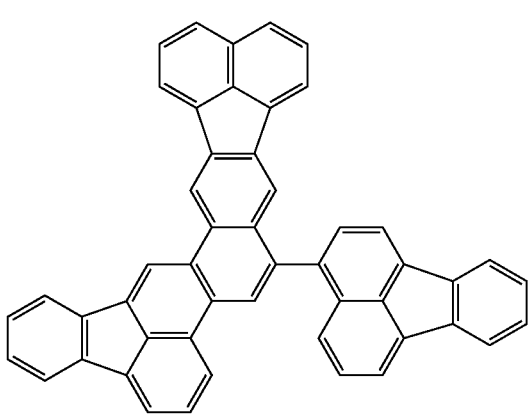
A25
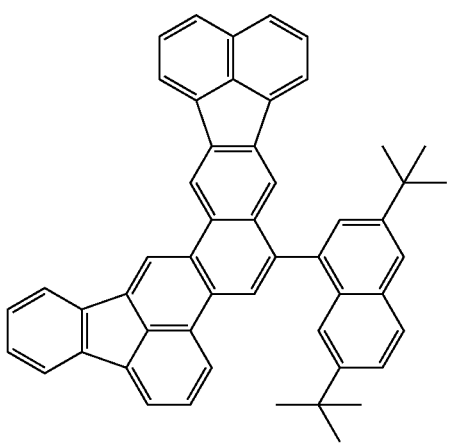

A26
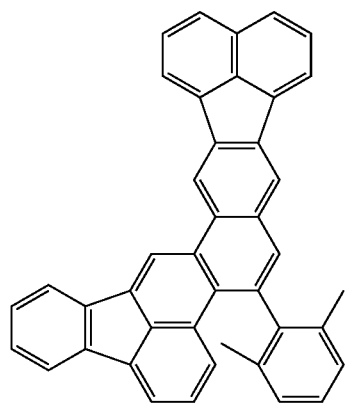
A27
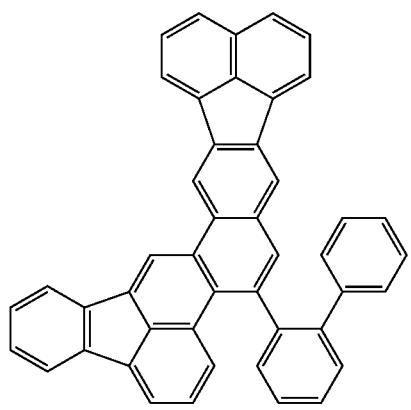
A28
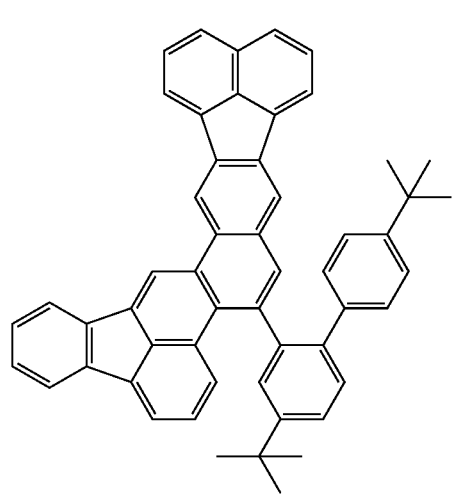
[Chem. 8]
B1
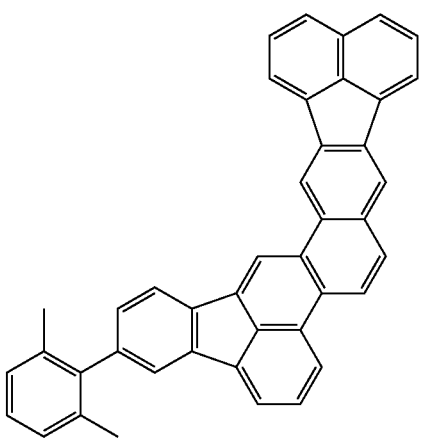
B2
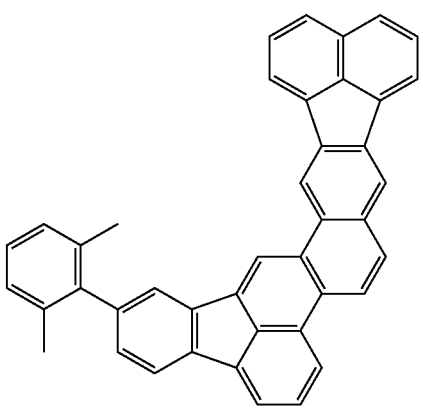
B3
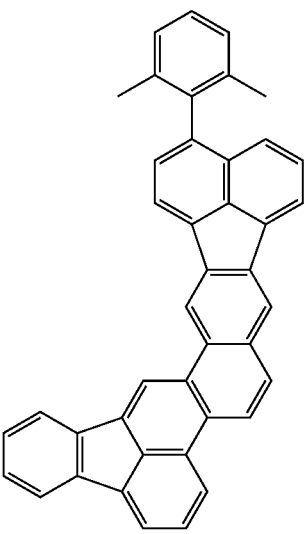

B4
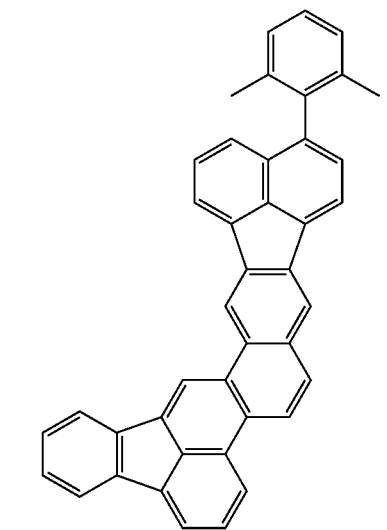
B5
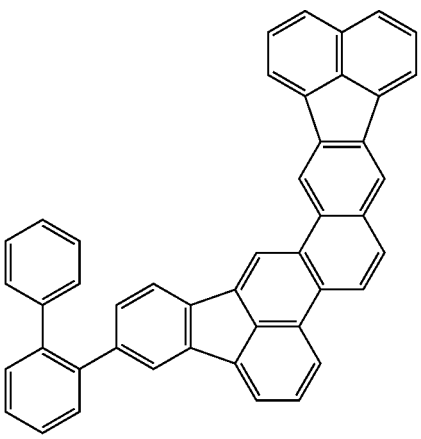
B6
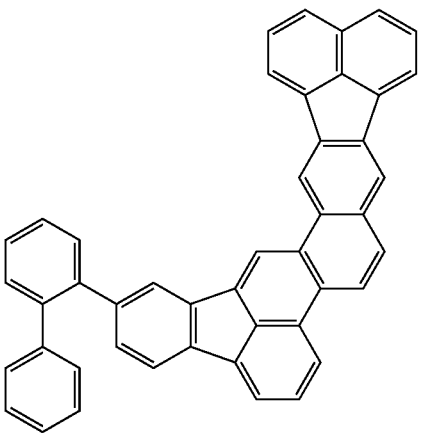
B7
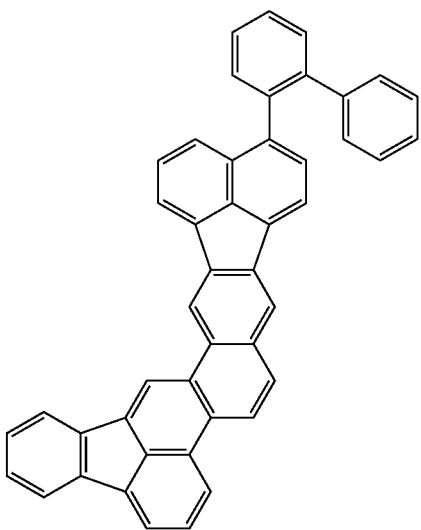
B8
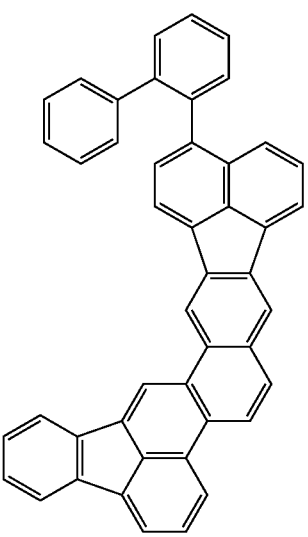
B9
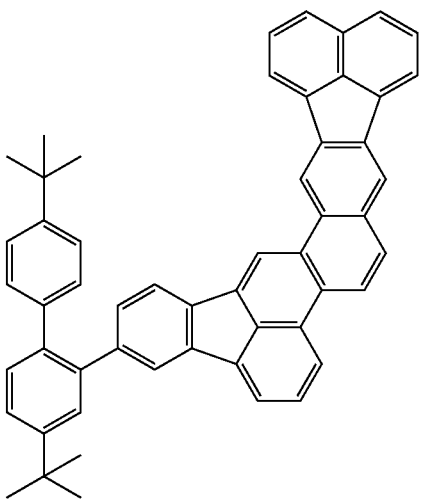

-continued
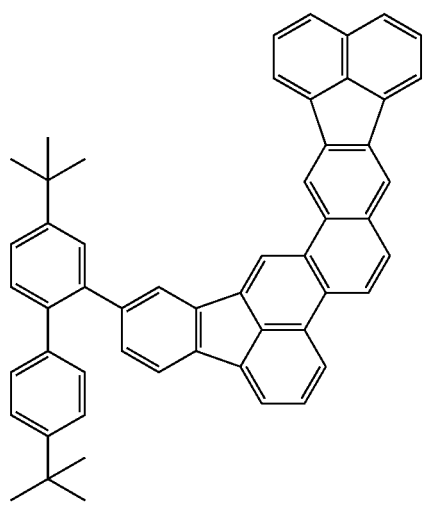
B10
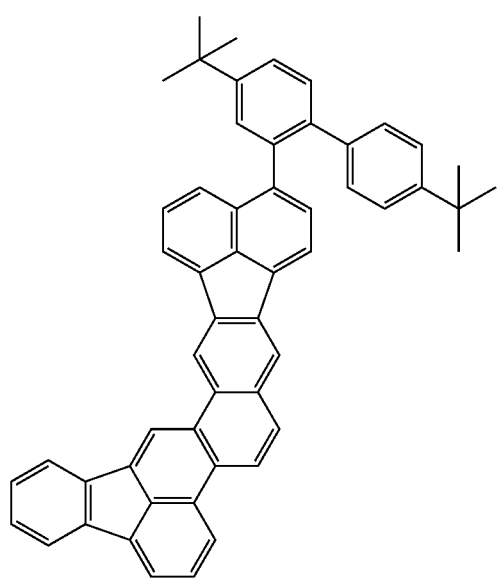
B12
[Chem. 9]
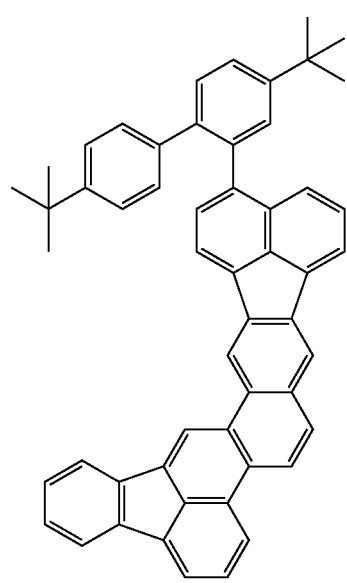
B11
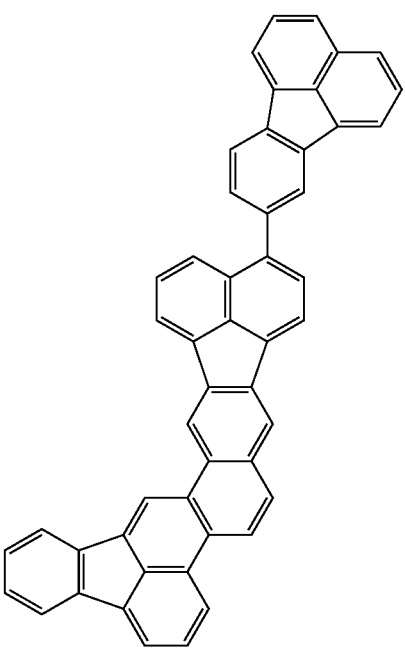
B13

-continued
B14
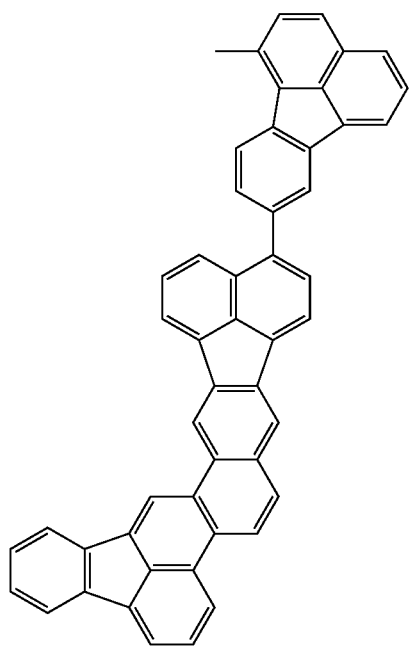
B15
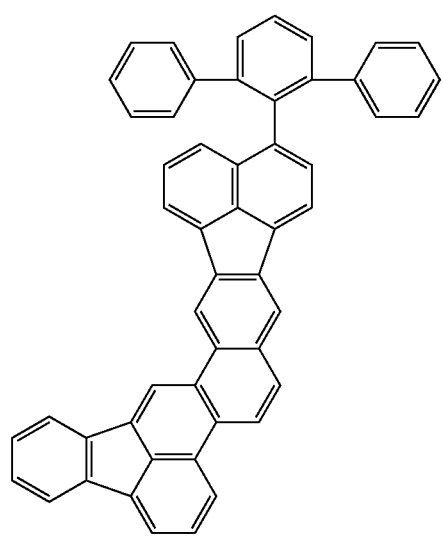
B16
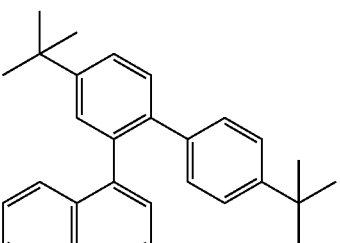
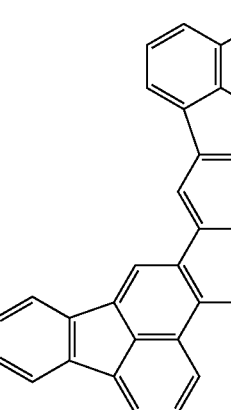
B17
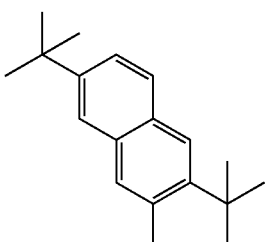

-continued
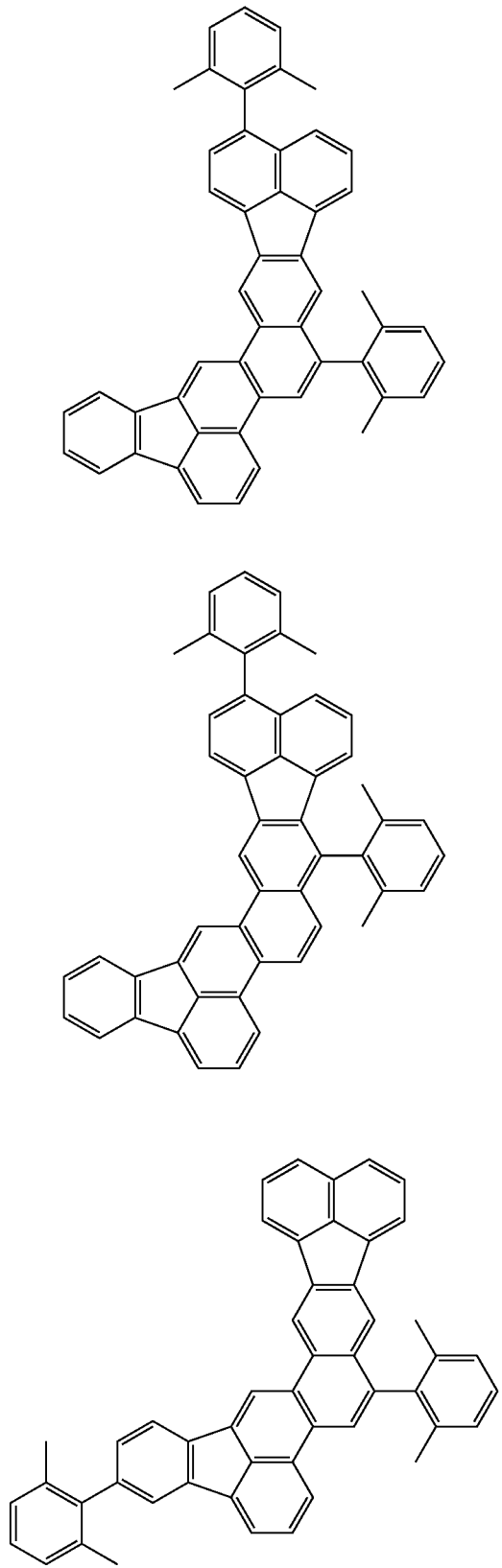
C1
C2
C3
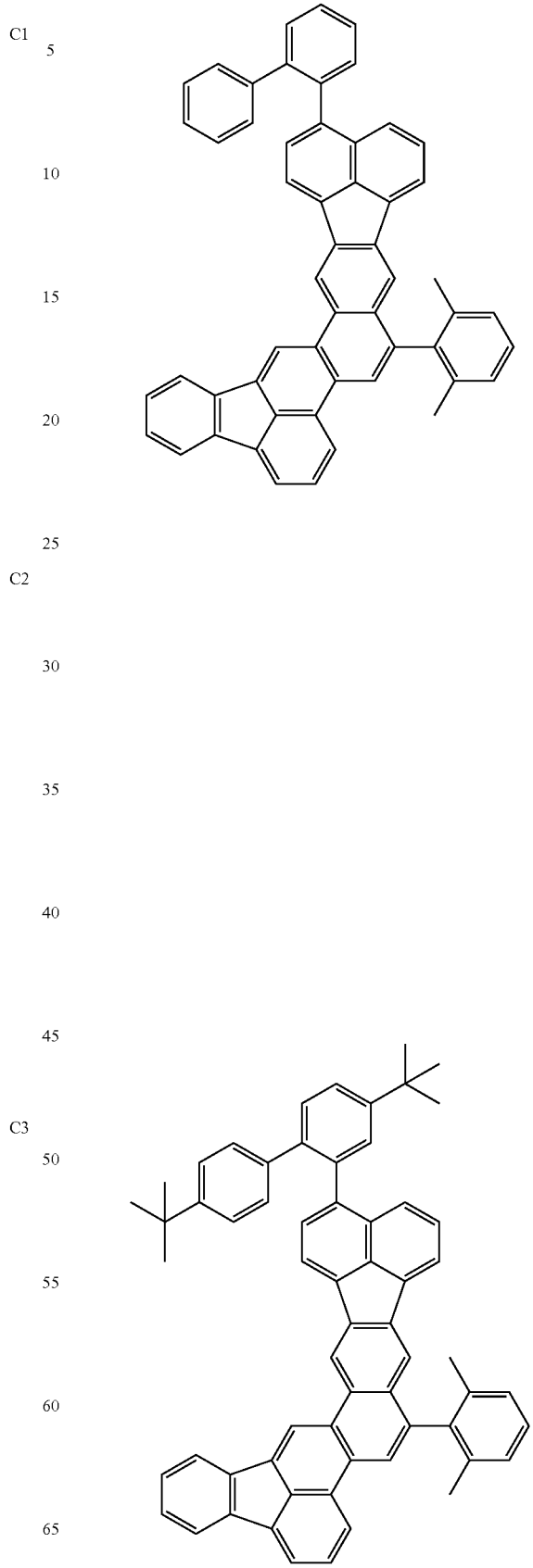
C4
C5

-continued
C6
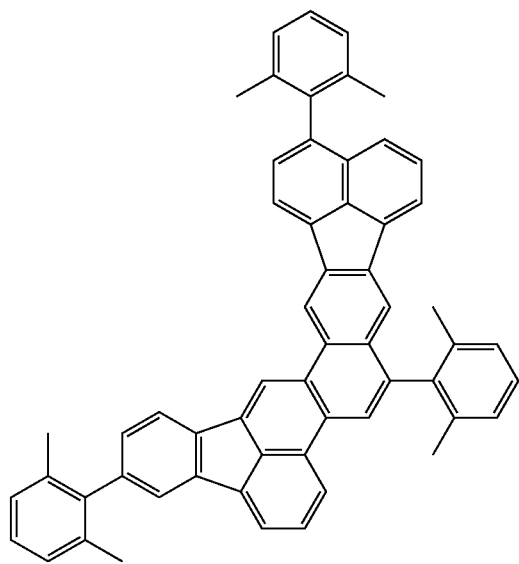
C7
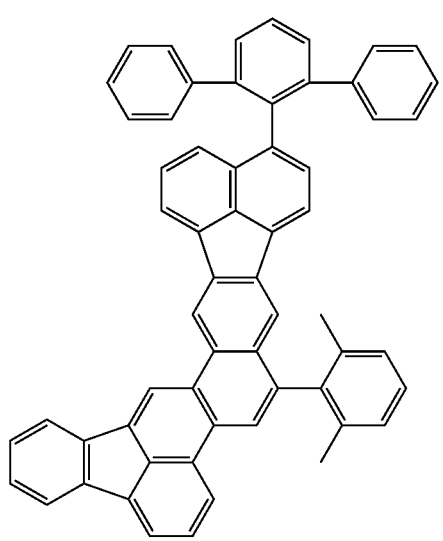
C8
-continued
C9
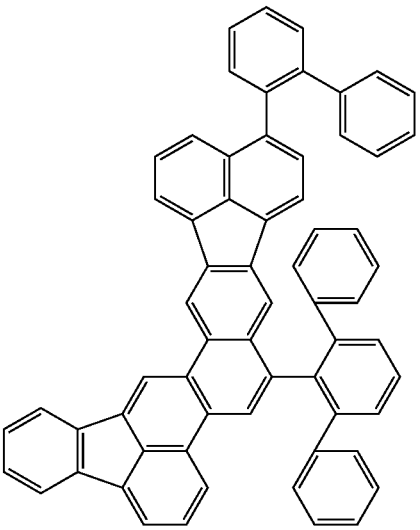
C10
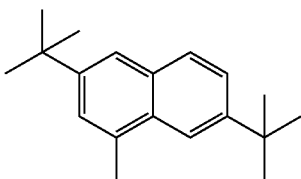
[Chem. 11]
C11
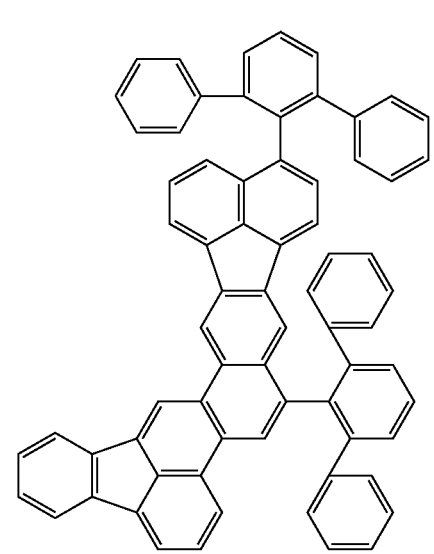

C12
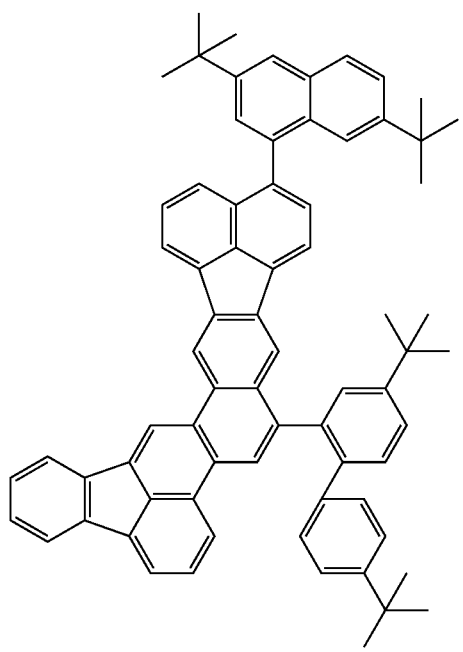
C14
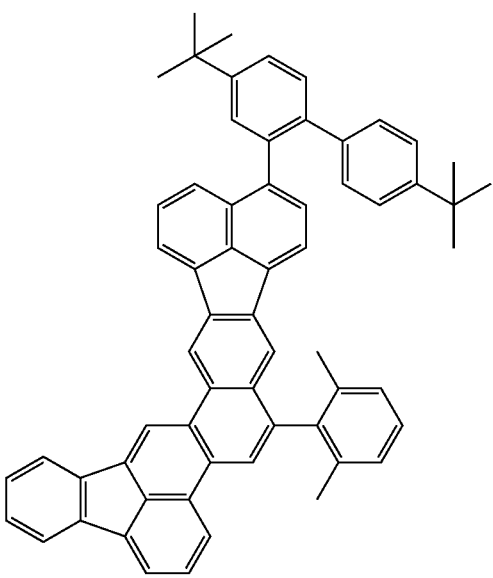
C13
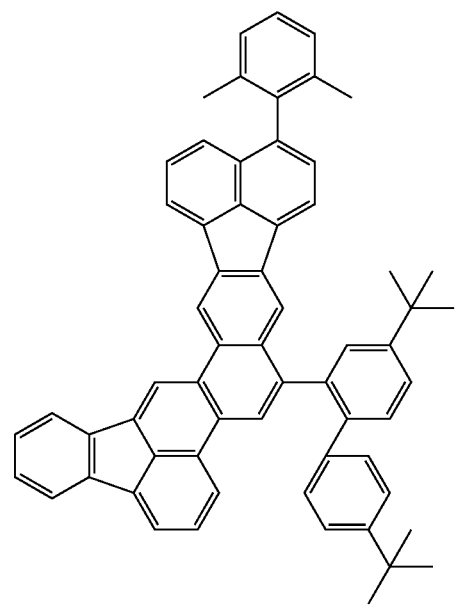
C15
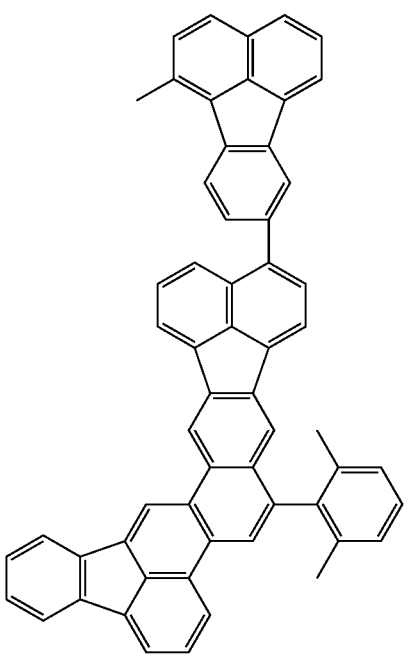

[Chem.12]
D1
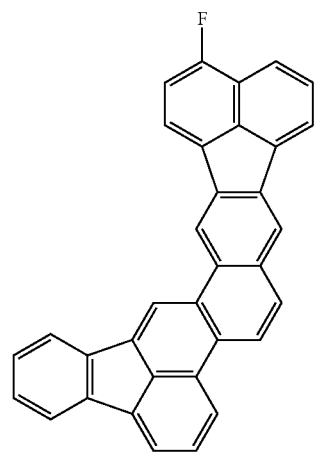
D2
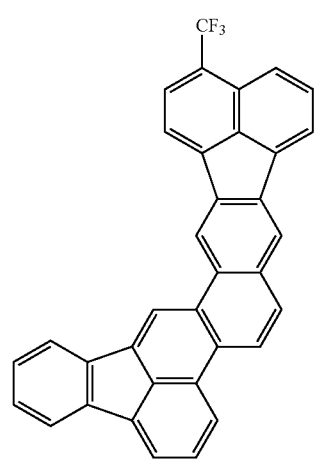
D3
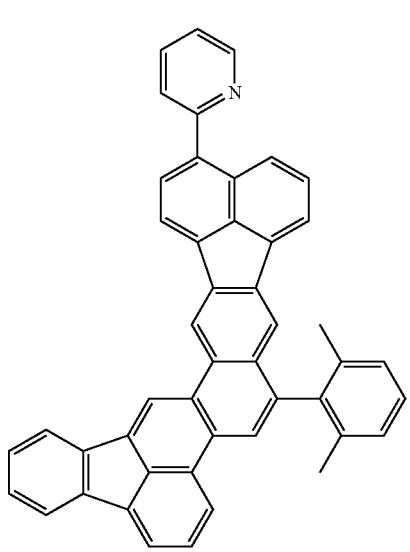
D4
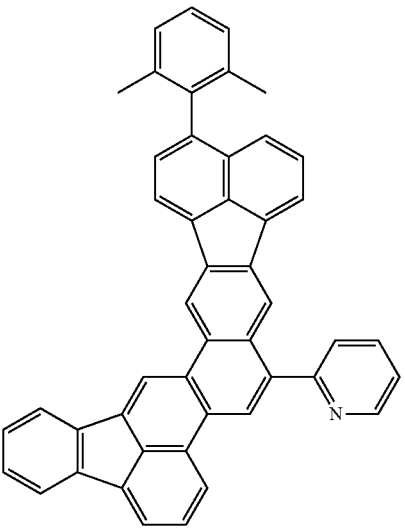
D5
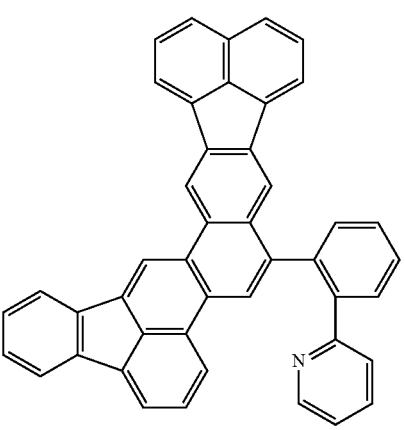
D6
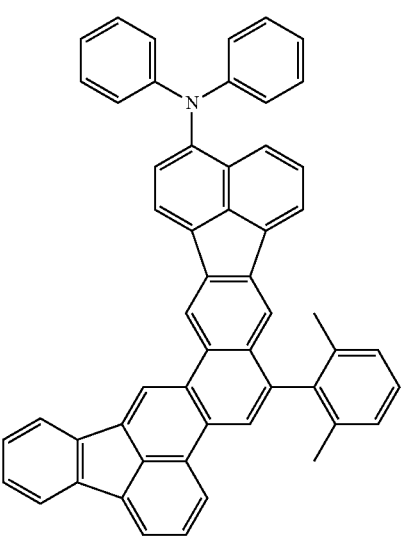

D7

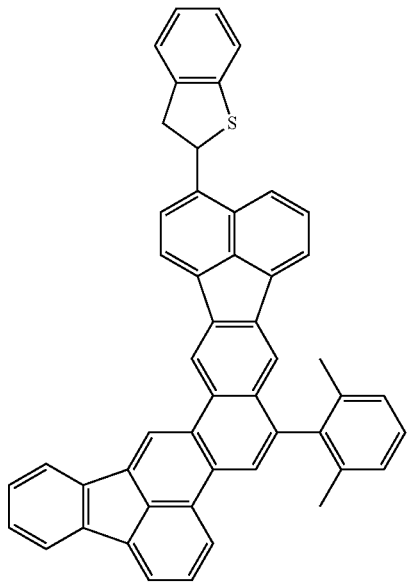

D8

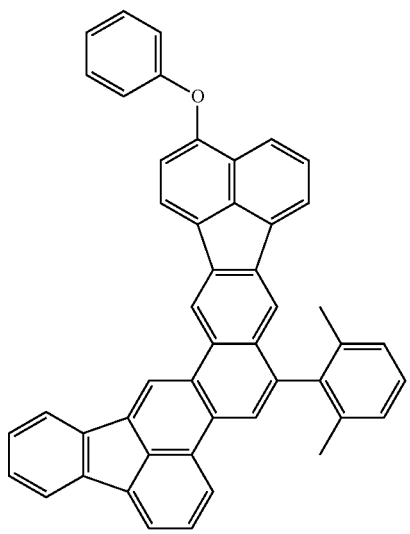

Properties of Compounds Exemplified

The A group of the exemplary compounds has a substituent at $R_{12}$, $R_{13}$, $R_{14}$, or $R_{15}$ on the basic skeleton. The basic skeleton of compounds according to embodiments of the present invention has high flatness and therefore possibly causes intermolecular stacking. Thus, the introduction of a steric hindrance group near the center of the basic skeleton ($R_{12}$, $R_{13}$, or $R_{15}$) can prevent intermolecular stacking.

A9 and A12 of the A group have a phenyl group at $R_{13}$. The phenyl group at $R_{13}$ may have another phenyl group or an alkyl group. The alkyl group may be a methyl group or a tertiary butyl group.

The B group has a substituent at $R_1$, $R_2$, $R_8$, or $R_9$. The basic skeleton of compounds according to embodiments of the present invention includes two five-membered ring fused. Because of the electron-withdrawing effect resulting from the five-membered ring structure, $R_1$, $R_2$, $R_8$, and $R_9$ of compounds according to embodiments of the present invention are substitution positions having high electrophilic reactivity. The introduction of a substituent having a lower elimination ability and chemical reactivity than a hydrogen atom into these substitution positions can improve the chemical stability of compounds according to embodiments of the present invention. B15 of the B group has a phenyl group at $R_9$. This phenyl group may have one or two or more phenyl groups.

The compounds of the C group have properties of both the A group and the B group. More specifically, the compounds of the C group are resistant to intermolecular stacking and have low reactivity.

As in the D group, the introduction of a substituent containing a heteroatom can greatly alter the oxidation potential of the molecule or alter intermolecular interaction. The introduction of a substituent containing a heteroatom can increase the maximum emission wavelength. When a compound having a substituent containing a heteroatom is used in an electron-transport, hole-transport, or hole-trap light-emitting material, the compound can be used in applications in which the compound is used at a high concentration of 100%.

Description of Synthetic Route

Examples of a synthetic route to organic compounds according to embodiments of the present invention will be described below. The following is a reaction formula.

The introduction of a substituent into an organic compound can involve the use of an intermediate in which a hydrogen atom at the substitution position is replaced with the substituent. Examples of the substituent include, but are not limited to, an alkyl group, a halogen atom, and an aryl group.

[Chem. 13]

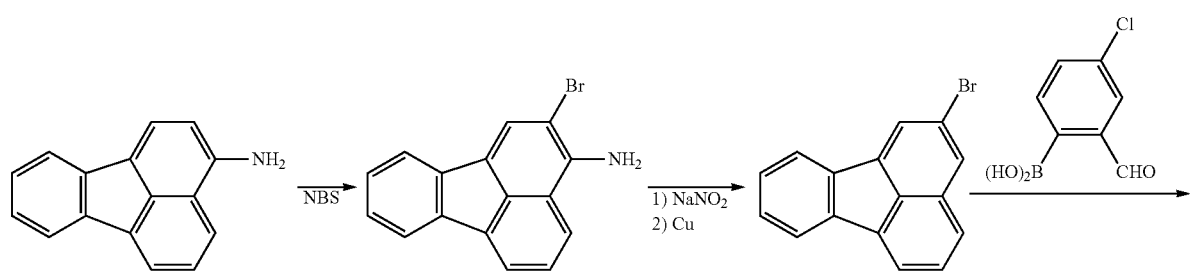

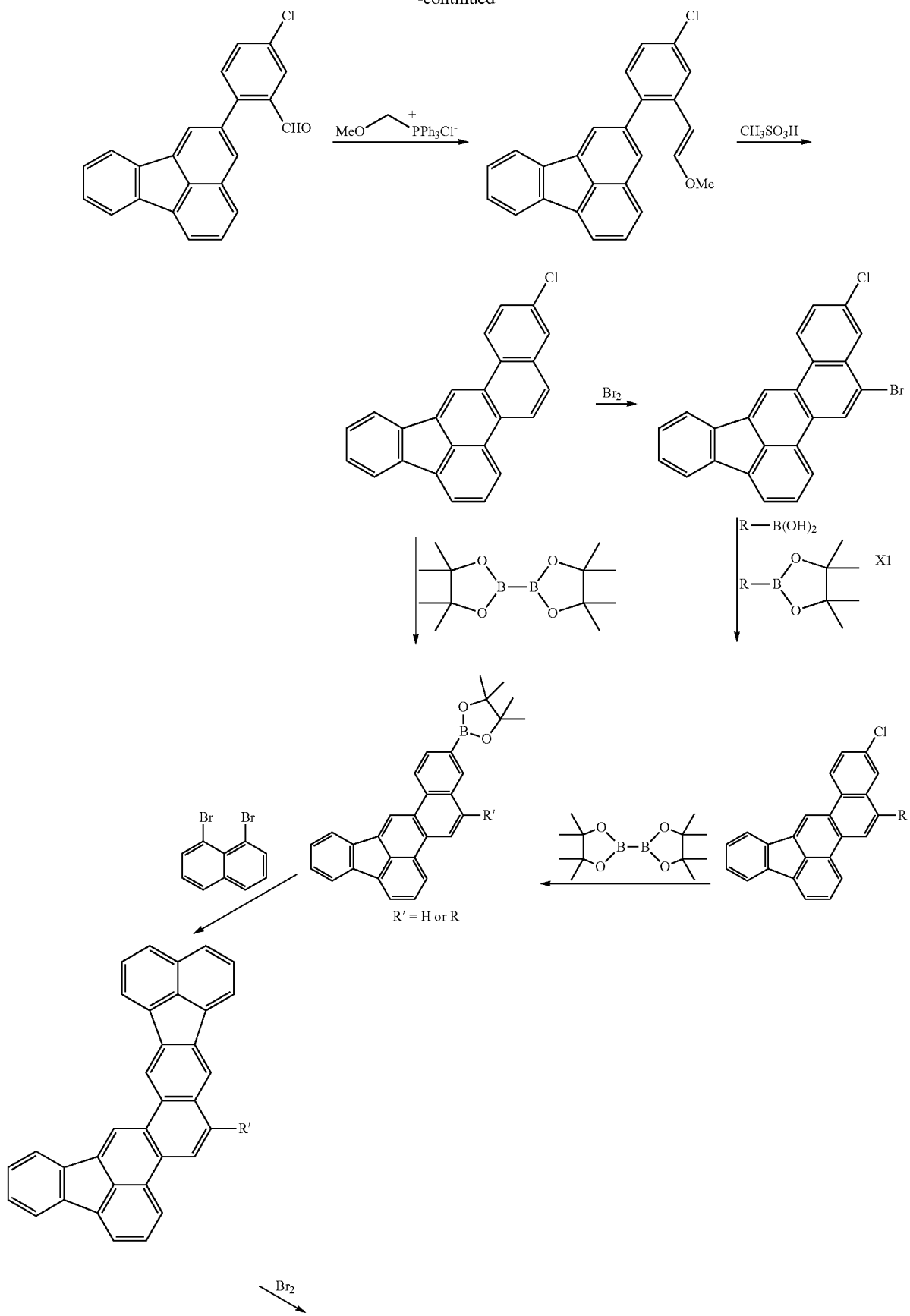

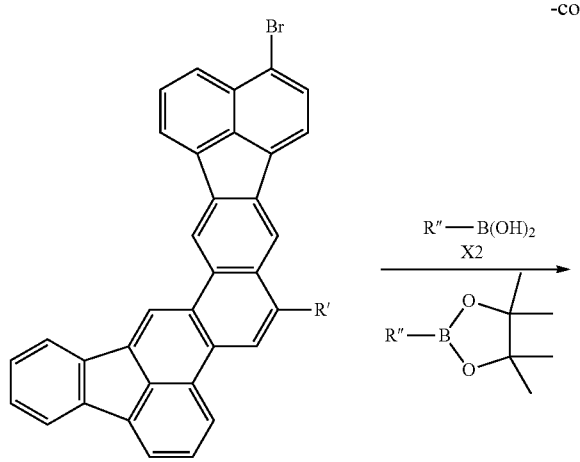 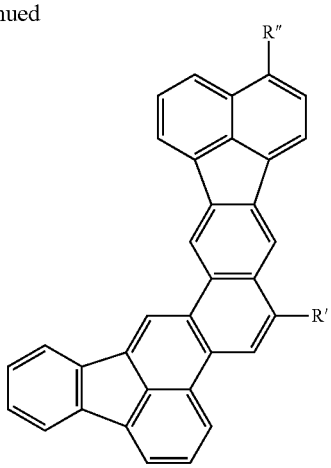
Other Organic Compounds and Raw Materials
X1 and X2 in the reaction formula can be varied to synthesize various organic compounds. Table 2 shows synthetic compounds as specific examples. The table also shows R and R″ of the raw materials X1 and X2 used for the production of the synthetic compounds.

TABLE 2
| | X1 | X2 | Synthetic compound | Exemplary compound No. |
|---|---|---|---|---|
| | | [Chem. 14] | | |
| Synthetic example 1 | 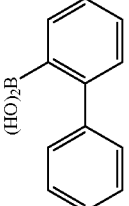 | — | 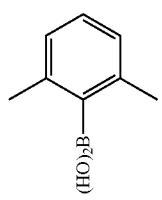 | A13 |
| Synthetic example 2 | 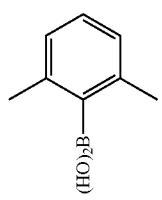 | — | 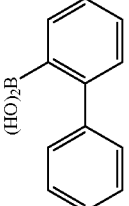 | A9 |

TABLE 2-continued

| Synthetic example | X1 | X2 | Synthetic compound | Exemplary compound No. |
|---|---|---|---|---|
| Synthetic example 3 | (structure) | — | (structure) | A23 |
| Synthetic example 4 | (structure) | — | (structure) | A24 |

TABLE 2-continued

| Synthetic example | X1 | X2 | Synthetic compound | Exemplary compound No. |
|---|---|---|---|---|
| Synthetic example 5 | | | | C15 |
| Synthetic example 6 | | | | C14 |
| Synthetic example 7 | | | | C13 |

[Chem. 15]

TABLE 2-continued
| | X1 | X2 | Synthetic compound | Exemplary compound No. |
|---|---|---|---|---|
| Synthetic example 8 | — | 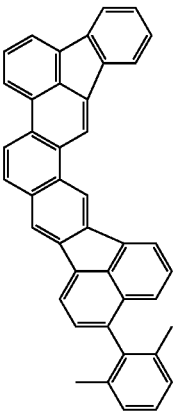 | 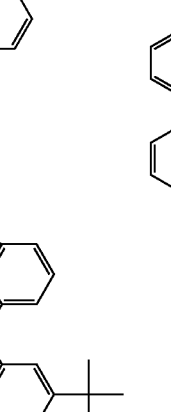 | B4 |
| Synthetic example 9 | — | 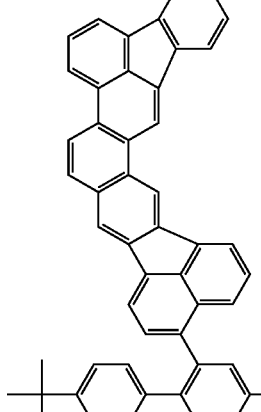 | 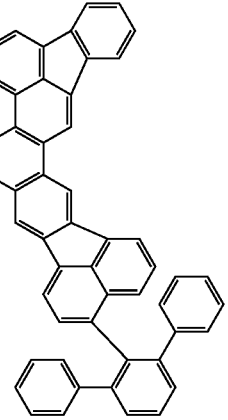 | B12 |
| Synthetic example 10 | — | 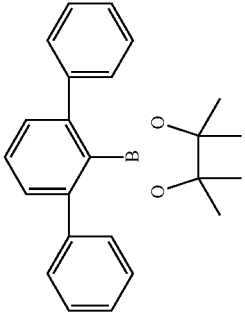 | 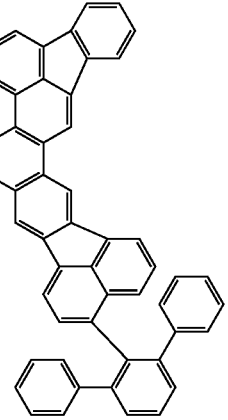 | B15 |

Description of Organic Light-Emitting Device

An organic light-emitting device according to an embodiment of the present invention will be described below.

An organic light-emitting device according to an embodiment of the present invention includes a pair of electrodes, an anode and a cathode, facing each other and an organic compound layer between the electrodes.

The ratio of the guest material to the host material is preferably 0.01% by weight or more and 20% by weight or less, more preferably 0.5% by weight or more and 10% by weight or less.

The following is an example of an organic light-emitting device that includes an organic compound according to an embodiment of the present invention.

An organic light-emitting device manufactured using an organic compound according to an embodiment of the present invention may include an anode, a light-emitting layer, and a cathode in this order on a substrate. Another organic light-emitting device manufactured using an organic compound according to an embodiment of the present invention may include an anode, a hole-transport layer, an electron-transport layer, and a cathode in this order. Still another organic light-emitting device may include an anode, a hole-transport layer, a light-emitting layer, an electron-transport layer, and a cathode in this order. Still another organic light-emitting device may include an anode, a hole-injection layer, a hole-transport layer, a light-emitting layer, an electron-transport layer, and a cathode in this order. Still another organic light-emitting device may include an anode, a hole-transport layer, a light-emitting layer, a hole-exciton-blocking layer, an electron-transport layer, and a cathode in this order. These five multilayer organic light-emitting devices only have a basic structure. An organic light-emitting device that includes an organic compound according to an embodiment of the present invention is not limited to these devices. For example, an insulating layer, an adhesive layer, or an interference layer may be disposed at an interface between an electrode and an organic compound layer. An electron-transport layer or a hole-transport layer may be formed of two sublayers having different ionization potentials.

An organic compound having the general formula (1) according to an embodiment of the present invention may be used in an organic compound layer of a light-emitting device having any layer structure. The light-emitting device may be of a top emission type in which light is extracted from an electrode on the substrate side, a bottom emission type in which light is extracted from the side opposite the substrate, or a top and bottom emission type in which light is extracted from both sides.

In addition to organic compounds according to embodiments of the present invention, conventionally known low-molecular-weight and high-molecular-weight compounds may be used if necessary. More specifically, an organic compound according to an embodiment of the present invention may be used in combination with a hole-injecting or hole-transport compound, a host material, a light-emitting compound, an electron-injecting compound, or an electron-transport compound.

Examples of these compounds will be described below.

It is desirable that the hole-injecting compound or the hole-transporting compound be a material having high hole mobility. Examples of the low-molecular-weight and high-molecular-weight materials having hole-injection ability or hole-transport ability include, but are not limited to, triarylamine derivatives, phenylenediamine derivatives, stilbene derivatives, phthalocyanine derivatives, porphyrin derivatives, polyvinylcarbazole, polythiophene, and other electroconductive polymers.

[Chem. 16]

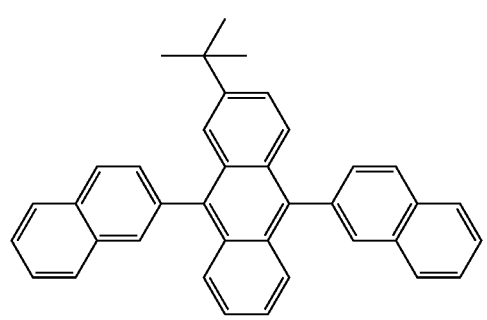

E1

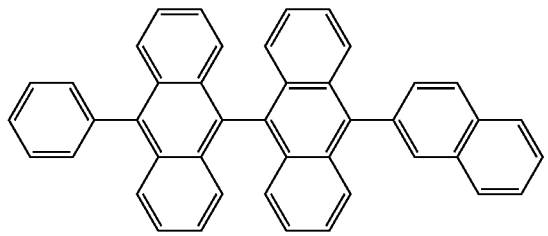

E2

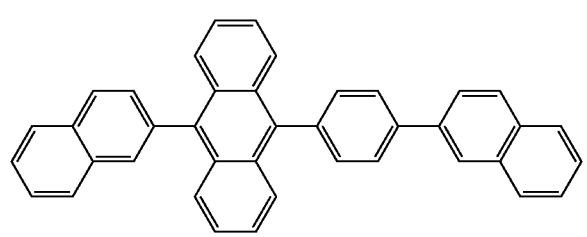

E3

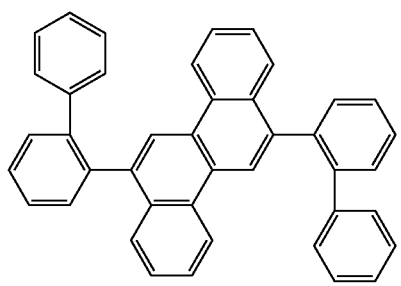

E4

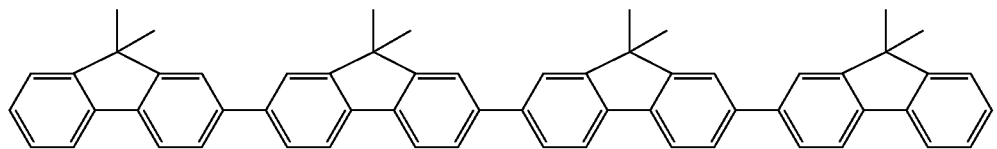

E5

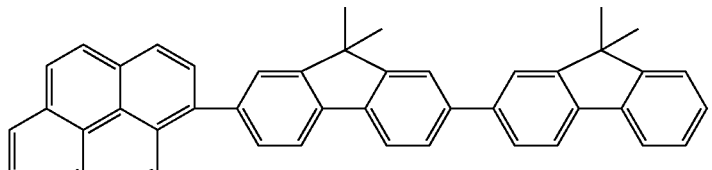

E6

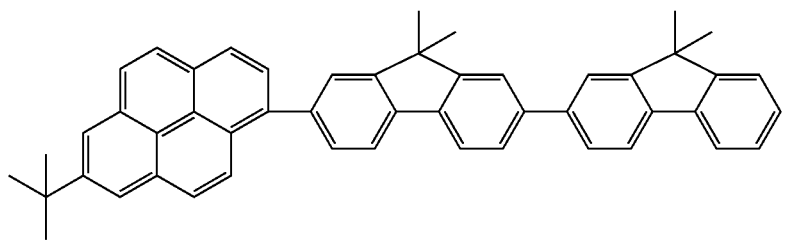

E7

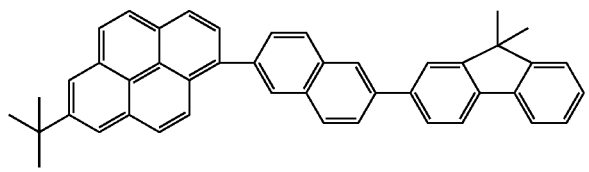

E8

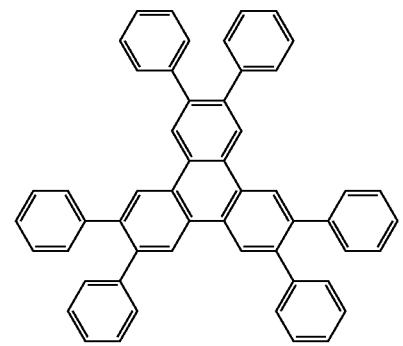

E9

Other examples of the host material include, but are not limited to, fused-ring compounds (for example, fluorene derivatives, naphthalene derivatives, anthracene derivatives, pyrene derivatives, carbazole derivatives, quinoxaline derivatives, and quinoline derivatives), organic aluminum complexes, such as tris(8-quinolinolato) aluminum, Zn complexes, triphenylamine derivatives, and polymer derivatives, such as polyfluorene derivatives and polyphenylene derivatives.

Examples of the compound having electron-injection ability or electron-transport ability include, but are not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes. These materials may be used in combination with an alkali metal or an alkaline-earth metal, such as LiF, KF, $Cs_2Co_3$, or CsF.

It is desirable that the material for the anode have a work function as large as possible. Examples of the anode material include, but are not limited to, metallic elements, such as gold, platinum, silver, copper, nickel, palladium, cobalt, selenium, vanadium, and tungsten, alloys of these metallic elements, and metal oxides, such as tin oxide, zinc oxide, indium oxide, indium tin oxide (ITO), and indium zinc oxide. Examples of the anode material also include, but are not limited to, electroconductive polymers, such as polyaniline, polypyrrole, and polythiophene. These electrode substances may be used alone or in combination. The anode may have a monolayer or multilayer structure.

It is desirable that the material for the cathode have a work function as low as possible. Examples of the cathode material include, but are not limited to, alkali metals, such as lithium, alkaline-earth metals, such as calcium, and metallic elements, such as aluminum, titanium, manganese, silver, lead, and chromium. Examples of the cathode material also include, but are not limited to, alloys of these metallic elements, such as magnesium-silver, aluminum-lithium, and aluminum-magnesium. Metal oxides, such as indium tin oxide (ITO), may also be used. These electrode substances may be used alone or in combination. The cathode may have a monolayer or multilayer structure.

In an organic light-emitting device according to an embodiment of the present invention, a layer containing an organic compound according to an embodiment of the present invention and a layer containing another organic compound can be formed in the following manner. In general, a thin film is formed by a vacuum evaporation method, an ionized deposition method, sputtering, plasma chemical vapor deposition (CVD), or a known coating method (for example, spin coating, dipping, casting, a Langmuir-Blodgett (LB) method, or an ink jet method) using a solution in an appropriate solvent. A layer formed by a vacuum evaporation method or a solution coating method experiences little crystallization and has excellent temporal stability. In the film formation by a coating method, an organic compound according to an embodiment of the present invention can be used in combination with an appropriate binder resin.

Examples of the binder resin include, but are not limited to, a polyvinylcarbazole resin, a polycarbonate resin, a polyester resin, an ABS resin, an acrylic resin, a polyimide resin, a phenolic resin, an epoxy resin, a silicone resin, and a urea resin. These binder resins may be used alone as a homopolymer or a copolymer or may be used in combination. If necessary, an additive agent, such as a known plasticizer, antioxidant, and/or ultraviolet absorber, may be used.

Applications of Organic Light-Emitting Device

An organic light-emitting device according to an embodiment of the present invention can be used in display apparatuses and lighting apparatuses. An organic light-emitting device according to an embodiment of the present invention can also be used in exposure light sources of electrophotographic image-forming apparatuses and backlights of liquid crystal displays.

A display apparatus includes an organic light-emitting device according to an embodiment of the present invention in a display. The display includes pixels, which include an organic light-emitting device according to an embodiment of the present invention. The display apparatus can be used as an image display apparatus in personal computers (PCs).

The display apparatus may also be used in displays of image pickup devices, such as digital cameras and digital video cameras. The image pickup devices include the display and an image-capturing unit including an imaging optical system.

FIG. 1 is a schematic cross-sectional view of an image display apparatus that includes an organic light-emitting device in a pixel unit. This FIGURE illustrates two organic light-emitting devices and two TFTs. Each of the organic light-emitting devices is connected to a corresponding one of the TFTs.

An image display apparatus 3 includes TFT devices 38, which are switching devices, a substrate 31, a moisture-proof film 32, gate electrodes 33, gate-insulating films 34, semiconductor layers 35, drain electrodes 36, source electrodes 37, an insulating film 39, contact holes 310, anodes 311, organic layers 312, cathodes 313, a first protective layer 314, and a second protective layer 315.

The image display apparatus 3 includes the moisture-proof film 32 on the substrate 31, for example, made of glass. The moisture-proof film 32 protects the components disposed thereon (TFTs and organic layers). The moisture-proof film 32 may be formed of silicon oxide or a composite of silicon oxide and silicon nitride. The gate electrodes 33 are disposed on the moisture-proof film 32. The gate electrodes 33 can be formed of metal, such as Cr, by sputtering.

The gate-insulating films 34 cover the gate electrodes 33. The gate-insulating films 34 can be formed by plasma CVD or catalytic chemical vapor deposition (cat-CVD) of silicon oxide and subsequent patterning. The gate-insulating films 34 thus patterned corresponding to the TFTs are individually covered with the semiconductor layer 35. The semiconductor layers 35 can be formed by forming a silicon film by plasma CVD (and optionally annealing at a temperature of, for example, 290 degrees Celsius or more) and patterning the silicon film after the circuit shape.

The drain electrode 36 and the source electrode 37 are disposed on each of the semiconductor layers 35. Thus, each of the TFT devices 38 includes the gate electrode 33, the gate-insulating layer 34, the semiconductor layer 35, the drain electrode 36, and the source electrode 37. The TFT devices 38 are covered with the insulating film 39. The insulating film 39 includes the contact holes (through holes) 310, which connect the source electrodes 37 to the anodes 311 of the organic light-emitting devices. The anodes 311 are made of metal.

The organic layer 312 and the cathode 313 are formed on each of the anodes 311, constituting an organic light-emitting device functioning as a pixel. The organic layer 312 is a multilayer containing a light-emitting layer or a light-emitting monolayer. The first protective layer 314 and the second protective layer 315 may be formed to prevent the deterioration of the organic light-emitting devices.

The switching devices are not particularly limited and may be the TFT devices described above or metal-insulator-metal (MIM) devices.

EXAMPLES

Examples of the present invention will be described below. However, the present invention is not limited to these examples.

Example 1

Synthesis of Exemplary Compound A12

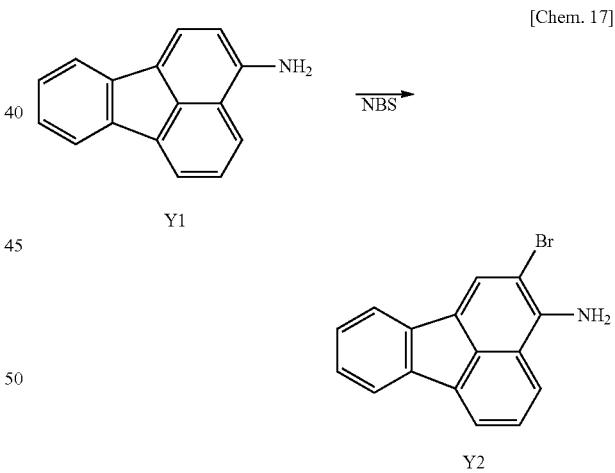

5.08 g (29 mmol) of N-bromosuccinimide (NBS) was added to 5.9 g (27 mmol) of Y1 in 250 ml of N,N-dimethylformamide at room temperature. After agitation for four hours, 100 ml of toluene and 250 ml of water were added to the solution, which was then extracted with toluene. The extract was washed twice with 100 ml each of water. After the organic phase was dried over magnesium sulfate, the solution was filtered. The filtrate was concentrated and recrystallized in toluene, yielding 6.6 g (yield=83%) of a brown solid Y2.

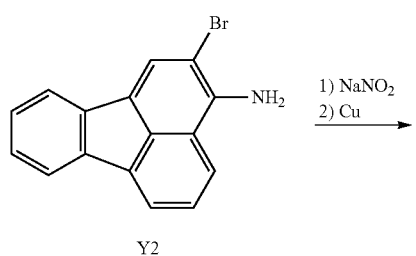

[Chem. 18]

Next, 3.5 g (12 mmol) of Y3, 2.8 g (15 mmol) of Y4, and 430 mg (0.37 mmol) of tetrakis(triphenylphosphine) palladium (0) in 60 ml of toluene, 30 ml of ethanol, and 30 ml of aqueous solution of sodium carbonate (20% by weight) was agitated at 90 degrees Celsius for four hours. After cooling, 100 ml of water was added to the solution. The solution was extracted with toluene. The extract was washed twice with 100 ml each of water. After the organic phase was dried over magnesium sulfate, the solution was filtered. The filtrate was concentrated, was purified by column chromatography (toluene:heptane=1:1), and was washed with methanol to yield 3.7 g (yield=88%) of a pale vermilion solid Y5.

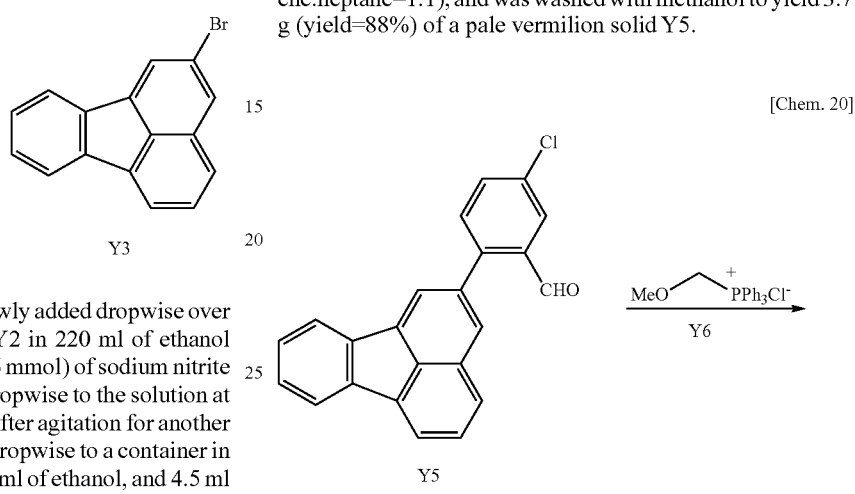

[Chem. 20]

Next, 6 ml of sulfuric acid was slowly added dropwise over 30 minutes to 6.5 g (22 mmol) of Y2 in 220 ml of ethanol cooled to 0 degrees Celsius. 1.8 g (26 mmol) of sodium nitrite in 2 ml of water was slowly added dropwise to the solution at 0 degrees Celsius over 30 minutes. After agitation for another 30 minutes, the solution was added dropwise to a container in which 1.7 g (26 mmol) of copper, 60 ml of ethanol, and 4.5 ml of sulfuric acid were refluxed for two hours in advance. The solution was refluxed for three hours, was cooled, and was extracted with chloroform. The organic phase was washed twice with 100 ml each of water and was dried over magnesium sulfate. After the solution was filtered, the filtrate was concentrated to yield a dark brown liquid. After the dark brown liquid was purified by column chromatography (heptane), washing with methanol yielded 3.7 g (yield=60%) of a pale yellow solid Y3.

[Chem. 19]

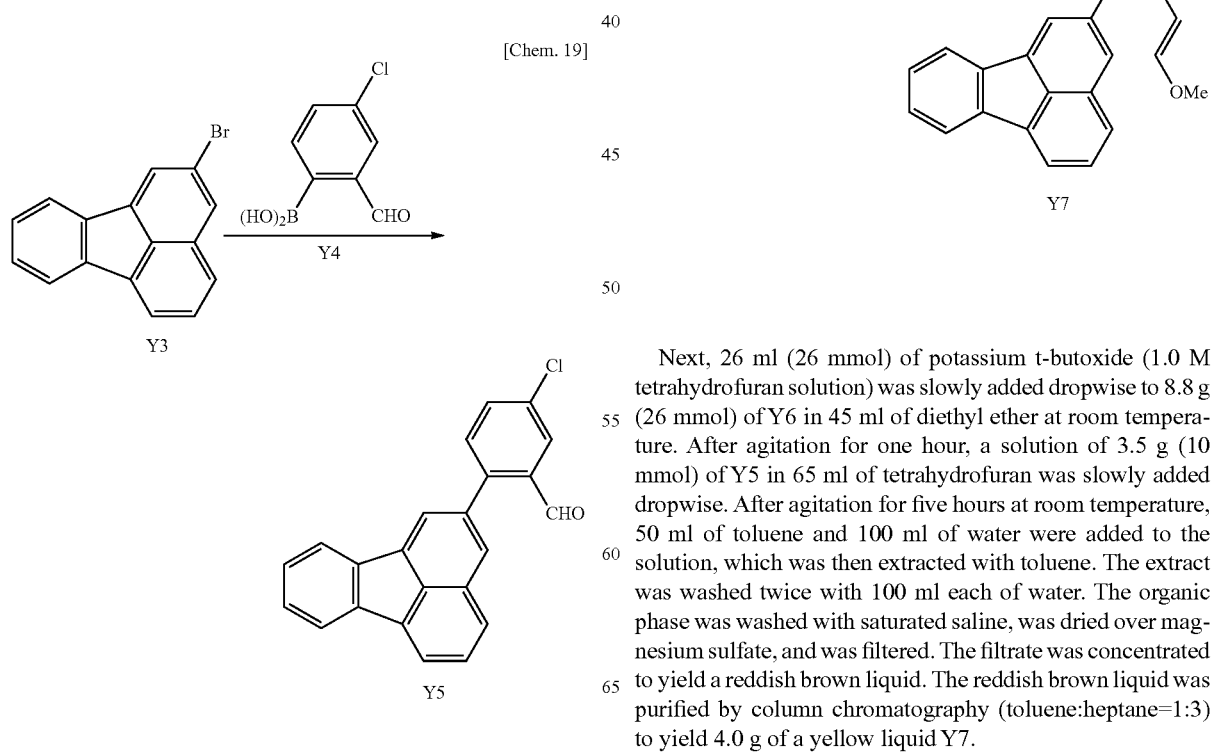

Next, 26 ml (26 mmol) of potassium t-butoxide (1.0 M tetrahydrofuran solution) was slowly added dropwise to 8.8 g (26 mmol) of Y6 in 45 ml of diethyl ether at room temperature. After agitation for one hour, a solution of 3.5 g (10 mmol) of Y5 in 65 ml of tetrahydrofuran was slowly added dropwise. After agitation for five hours at room temperature, 50 ml of toluene and 100 ml of water were added to the solution, which was then extracted with toluene. The extract was washed twice with 100 ml each of water. The organic phase was washed with saturated saline, was dried over magnesium sulfate, and was filtered. The filtrate was concentrated to yield a reddish brown liquid. The reddish brown liquid was purified by column chromatography (toluene:heptane=1:3) to yield 4.0 g of a yellow liquid Y7.

[Chem. 21]

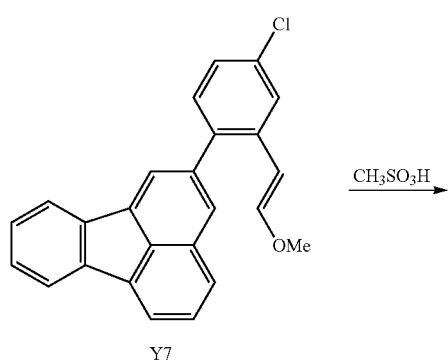

Y7

Next, 0.52 ml of methanesulfonic acid was slowly added dropwise to a solution of 4.0 g of Y7 in 60 ml of dichloromethane at room temperature. After agitation at room temperature for 17 hours, 200 ml of methanol was added to the solution. The resulting precipitate was filtered, was washed with methanol, and was dried at 80 degrees Celsius under vacuum to yield 3.2 g (a yield based on Y5=93%) of a light yellow solid Y8.

[Chem. 22]

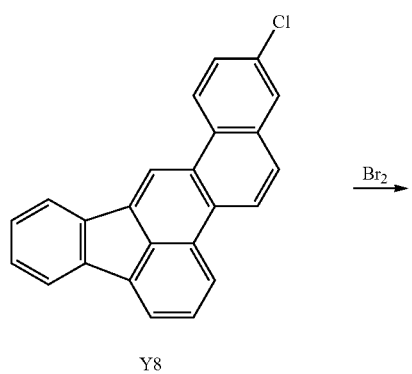

Next, a solution of bromine 0.16 ml (3.0 mmol) in 16 ml of dichloromethane was slowly added dropwise for 30 minutes to 1.0 g (3.0 mmol) of Y8 in 130 ml of chloroform cooled to 0 degrees Celsius. After agitation for 18 hours while heating to room temperature, 150 ml of methanol was added to the solution. The resulting precipitate was filtered and was washed with methanol to yield 1.2 g (yield=94%) of a light yellow solid Y9.

[Chem. 23]

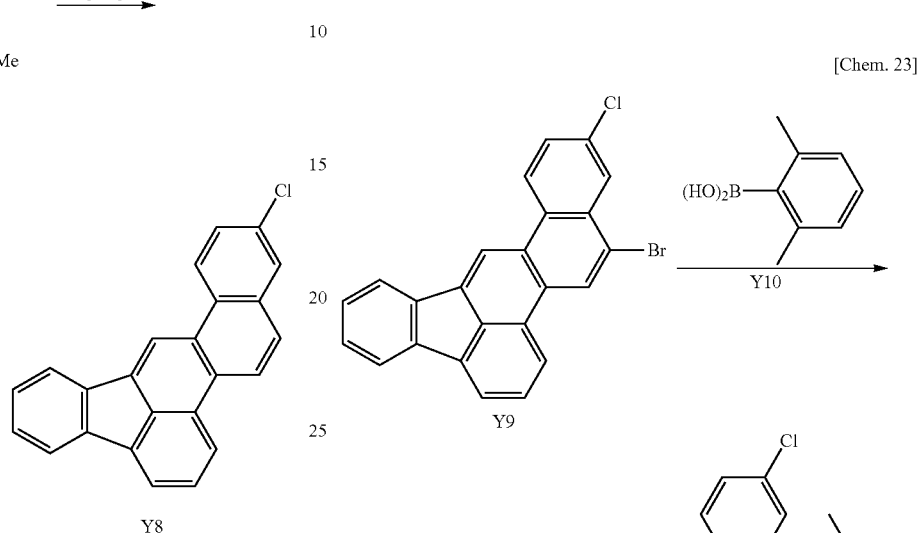

Next, 1.1 g (2.6 mmol) of Y9, 0.60 g (4.0 mmol) of Y10, and 180 mg (0.16 mmol) of tetrakis(triphenylphosphine) palladium (0) in 25 ml of toluene, 12 ml of ethanol, and 13 ml of aqueous solution of sodium carbonate (20% by weight) were agitated at 90 degrees Celsius for six hours. After cooling, 100 ml of water was added to the solution. The solution was extracted with toluene. The extract was washed twice with 100 ml each of water. The organic phase was washed with saturated saline, was dried over magnesium sulfate, and was filtered. The filtrate was concentrated. After purification by column chromatography (chloroform:heptane=1:5), recrystallization with toluene and ethanol yielded 0.68 g (yield=58%) of a light yellow solid Y11.

[Chem. 24]

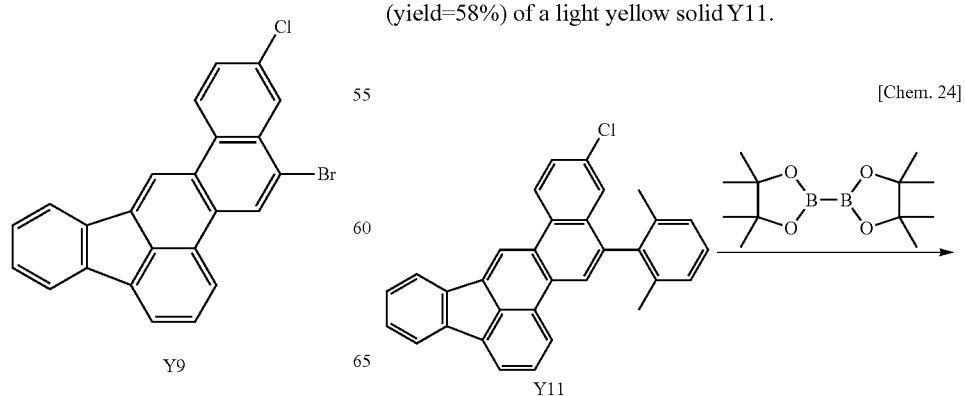

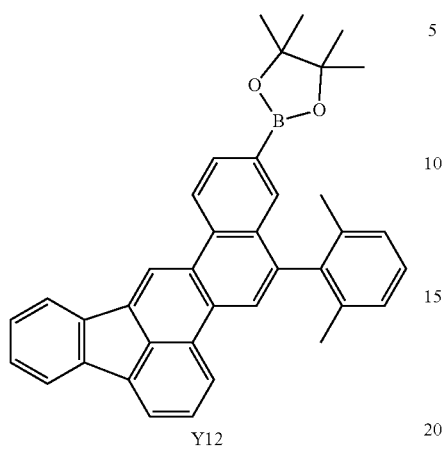

Y12

Next, 210 mg (0.23 mmol) of tris(dibenzylideneacetone) dipalladium (0) and 160 mg (0.57 mmol) of tricyclohexyl phosphine in 20 ml of 1,4-dioxane were agitated at room temperature for 15 minutes. 0.65 g (1.5 mmol) of Y11, 0.87 g (3.4 mmol) of bis(pinacolato)diboron, and 0.33 g (3.4 mmol) of potassium acetate were then added to the solution. The solution was then agitated at 95 degrees Celsius for three hours. After cooling, 100 ml of water was added to the solution. The solution was extracted with toluene. The extract was washed twice with 100 ml each of water. The organic phase was dried over magnesium sulfate and was filtered. The filtrate was concentrated to yield a black liquid. The black liquid was purified by column chromatography (chloroform:heptane=1:2) and was washed with methanol to yield 0.60 g (yield=77%) of a light yellow solid Y12.

[Chem. 25]

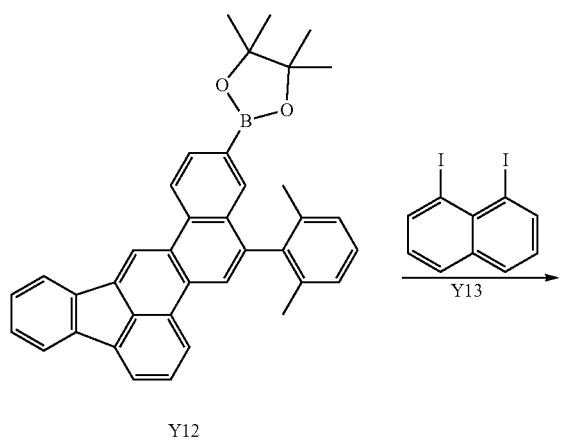

Y12

Y13

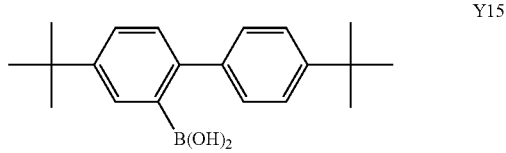

Y14

Next, 170 mg (0.19 mmol) of tris(dibenzylideneacetone) dipalladium (0) and 210 mg (0.75 mmol) of tricyclohexyl phosphine in 9 ml of N,N-dimethylformamide were agitated at room temperature for 15 minutes. 0.50 g (0.94 mmol) of Y12, 0.56 g (1.5 mmol) of Y13, and 1.4 ml (9.4 mmol) of 1,8-diazabicyclo[5.4.0]undec-7-ene (DBU) were added to the solution. The solution was agitated at 170 degrees Celsius for three hours. After cooling, 100 ml of water was added to the solution. The solution was extracted with toluene. The extract was washed twice with 100 ml each of water. The organic phase was dried over magnesium sulfate and was filtered. The filtrate was concentrated. After purification by column chromatography (chloroform:heptane=1:5), recrystallization with toluene yielded 33 mg (yield=7%) of a yellow solid Y14 (exemplary compound A12).

The emission spectrum of a $1*10^{-5}$ mol/L toluene solution of the exemplary compound A12 was measured by photoluminescence at an excitation wavelength of 350 nm with F-4500 manufactured by Hitachi, Ltd. The emission spectrum had the maximum intensity at 432 nm. The quantum yield of the solution measured with C9920 manufactured by Hamamatsu Photonics K.K. was 0.76.

Example 2

Synthesis of Exemplary Compound A9

Y17 (exemplary compound A9) was prepared by the same reactions and purification as in Example 1 except that the organic compound Y10 and Y13 were replaced with Y15 and Y16, respectively.

[Chem. 26]

Y15

-continued

Y16

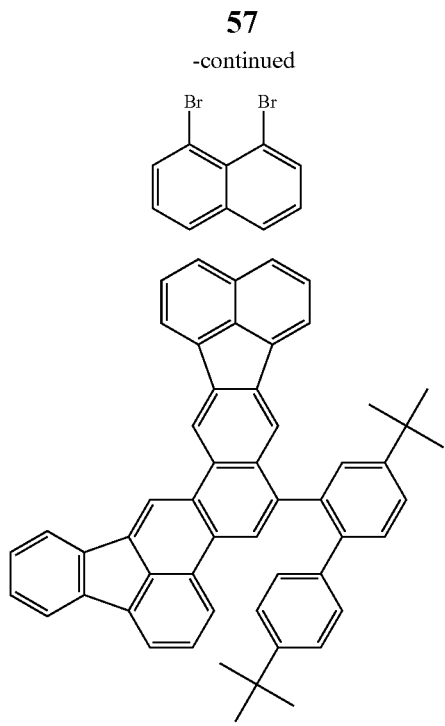

The emission spectrum of a 1*10⁻⁵ mol/L toluene solution of the exemplary compound A9 was measured by photoluminescence at an excitation wavelength of 350 nm with F-4500 manufactured by Hitachi, Ltd. The emission spectrum had the maximum intensity at 441 nm. The quantum yield of the solution measured with C9920 manufactured by Hamamatsu Photonics K.K. was 0.78.

Example 3

Synthesis of Exemplary Compound B15

Y24 (exemplary compound B15) was prepared by the same reactions and purification as in Examples 1 and 2 except that the organic compound Y11 in Example 1 and the organic compound Y21 in Example 2 were replaced with Y8 and Y23, respectively.

[Chem. 27]

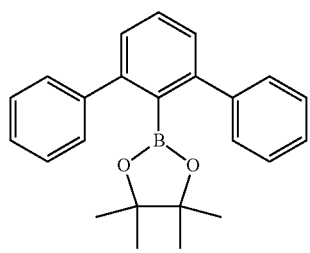

Y23

-continued

Y17

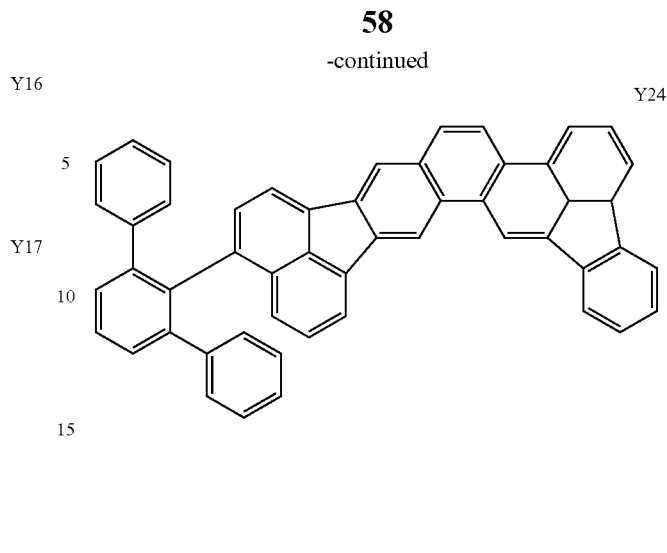

Y24

The emission spectrum of a 1*10⁻⁵ mol/L toluene solution of the exemplary compound B15 was measured by photoluminescence at an excitation wavelength of 350 nm with F-4500 manufactured by Hitachi, Ltd. The emission spectrum had the maximum intensity at 442 nm. The quantum yield of the solution measured with C9920 manufactured by Hamamatsu Photonics K.K. was 0.80.

Example 4

Synthesis of Exemplary Compound C13

[Chem. 28]

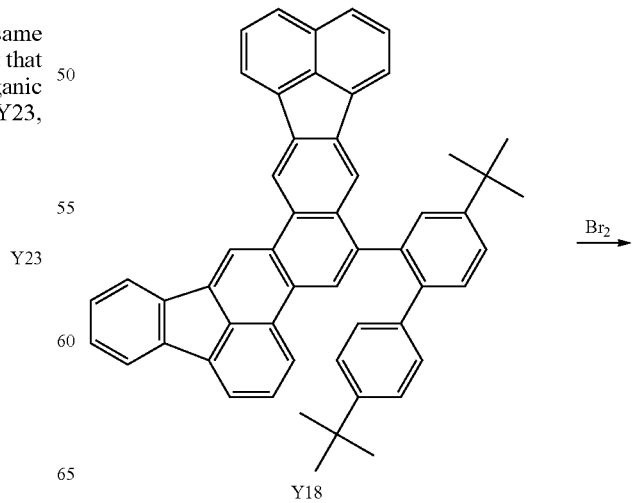

Y18

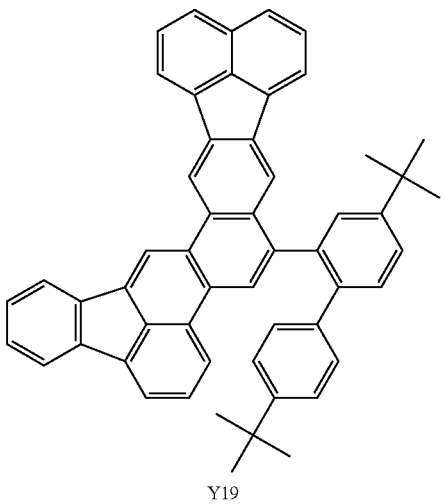

Y19

A solution of 0.008 ml (0.16 mmol) of bromine in 0.16 ml of dichloromethane was slowly added dropwise to 110 mg (0.16 mmol) of Y18 in 2 ml of chloroform at room temperature. After agitation for 18 hours, 100 ml of methanol was added to the solution. The resulting precipitate was filtered and was washed with methanol to yield 0.14 g (yield=95%) of a yellow solid Y19.

[Chem. 29]

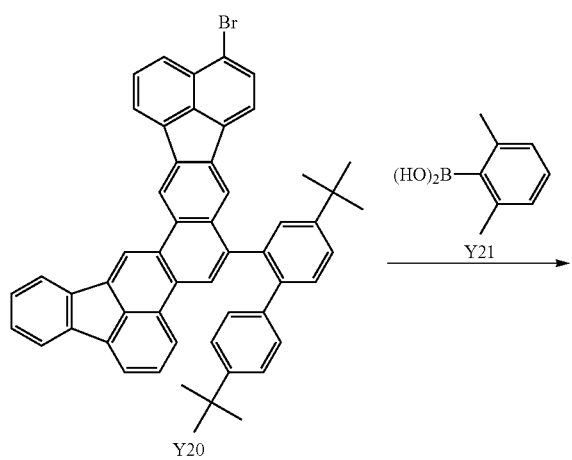

Y20

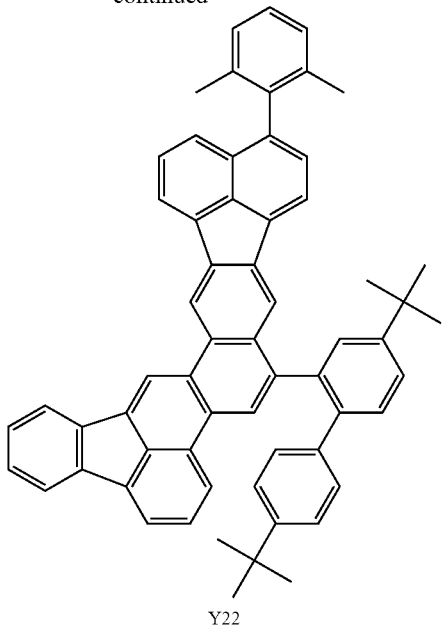

Y22

Next, 0.14 g (0.15 mmol) of Y20, 27 mg (0.18 mmol) of Y21, 9 mg (0.023 mmol) of 2-dicyclohexylphosphino-2',6'-dimethoxybiphenyl, 3 mg (0.015 mmol) of palladium acetate, and 64 mg (0.30 mmol) of potassium phosphate in 2 ml of toluene and 0.2 ml of distilled water were agitated at 95 degrees Celsius for three hours. After cooling, 100 ml of water was added to the solution. The solution was extracted with toluene. The extract was washed twice with 100 ml each of water. The organic phase was washed with saturated saline, was dried over magnesium sulfate, and was filtered. The filtrate was concentrated. After purification by column chromatography (chloroform:heptane=1:4), recrystallization with toluene, heptane, and ethanol yielded 40 mg (yield=34%) of a yellow solid Y22 (exemplary compound C13).

The emission spectrum of a $1*10^{-5}$ mol/L toluene solution of the exemplary compound C13 was measured by photoluminescence at an excitation wavelength of 350 nm with F-4500 manufactured by Hitachi, Ltd. The emission spectrum had the maximum intensity at 446 nm. The quantum yield of the solution measured with C9920 manufactured by Hamamatsu Photonics K.K. was 0.80.

Example 5

The present example describes the fifth example of the multilayer organic light-emitting devices described above (anode/hole-injection layer/hole-transport layer/light-emitting layer/hole-exciton-blocking layer/electron-transport layer/cathode). An ITO film having a thickness of 100 nm was formed on a glass substrate by sputtering and was patterned by photolithography. The following organic layers and electrode layers were continuously formed on the ITO substrate in a vacuum chamber at $10^{-5}$ Pa by vacuum evaporation with resistance heating. The emission area was 3 mm². A device thus fabricated was sealed in an inert atmosphere with a glass cap containing a moisture absorbent.

Hole-injection layer (40 nm): F-1
Hole-transport layer (10 nm): F-2
Light-emitting layer (30 nm): E-7 as a host material and the exemplary compound A9 as a guest material (the weight ratio of the guest material to the host material was 5%)

Electron-transport layer (40 nm): F-3
Metal electrode layer 1 (0.5 nm): LiF
Metal electrode layer 2 (100 nm): Al

[Chem. 30]

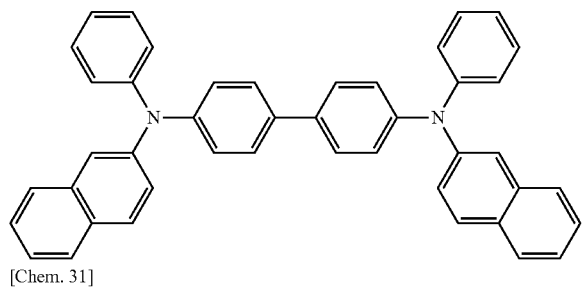

F1

[Chem. 31]

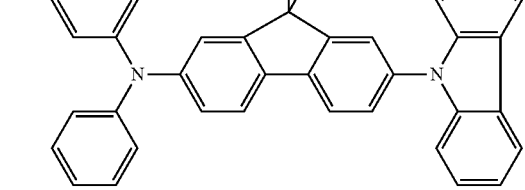

F2

[Chem. 32]

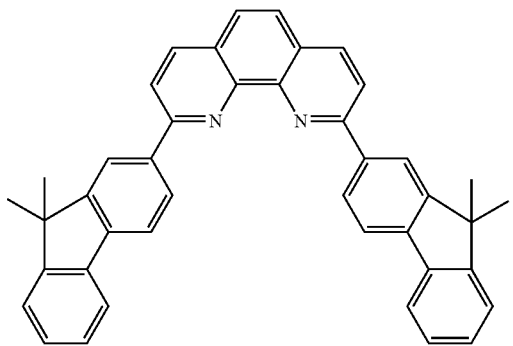

F3

The current-voltage characteristics of the EL device were measured with an ammeter 2700 manufactured by Keithley Instruments, Inc. The luminance of the EL device was measured with BM7-fast manufactured by Topcon Co.

Example 6

An organic EL device was fabricated in the same manner as in Example 5 except that the guest material for the light-emitting layer was changed to A12.

Example 7

An organic EL device was fabricated in the same manner as in Example 5 except that the guest material for the light-emitting layer was changed to B15.

Example 8

An organic EL device was fabricated in the same manner as in Example 5 except that the guest material for the light-emitting layer was changed to C13.

Example 9

An organic EL device was fabricated in the same manner as in Example 5 except that a hole-blocking layer E8 was disposed between the light-emitting layer and the electron-transport layer.

Table 3 shows the luminous efficiencies of Examples 5 to 9 at 10 mA/cm$^2$.

TABLE 3

[Chem. 33]

| | Host material | Guest material | Electron-transport layer | Luminous efficiency (cd/A) |
|---|---|---|---|---|
| Example 5 | E7 | A9 | F3 | 5.0 |
| Example 6 | E7 | A12 | F3 | 4.5 |
| Example 7 | E7 | B15 | F3 | 5.6 |
| Example 8 | E7 | C13 | F3 | 5.6 |
| Example 9 | E7 | A9 | E8/F3 | 7.2 |

Example 10

In the present example, a top emission type organic EL device was fabricated.

An Al film was formed on a transparent glass substrate by sputtering. An indium zinc oxide (IZO) film having a thickness of 80 nm was formed as a transparent electrode on the Al film by sputtering. A pixel was separated by an acrylic resin, fabricating a substrate having an electrode area of 3 mm$^2$. The following organic layers were formed on the ITO substrate in a vacuum chamber at $10^{-5}$ Pa by vacuum evaporation with resistance heating. The following transparent electrode layer was formed by sputtering.

A device thus fabricated was sealed in an inert atmosphere with a glass cap containing a moisture absorbent.

Hole-injection layer (20 nm): F-1
Hole-transport layer (10 nm): F-2
Light-emitting layer (30 nm): E-7 as a host material and the exemplary compound A9 as a guest material (the weight ratio of the guest material to the host material was 5%)
Electron-transport layer (10 nm): E8
Electron-injection layer (50 nm): Co-evaporation of F-3 and cesium carbonate (the weight ratio of cesium carbonate to F-3 was 3% by weight)
Transparent electrode layer (30 nm): IZO The luminous efficiency of this device measured in the same manner as in Example 5 was 3.2 cd/A.

As described above, an organic compound according to the present invention is a novel compound that has a high quantum yield and light-emitting properties suitable for a blue region. An organic light-emitting device that contains the organic compound has excellent light-emitting properties.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-031659, filed Feb. 16, 2010, which is hereby incorporated by reference herein in its entirety.

The invention claimed is:
1. An organic compound represented by the following general formula (1):

[Chem. 2]

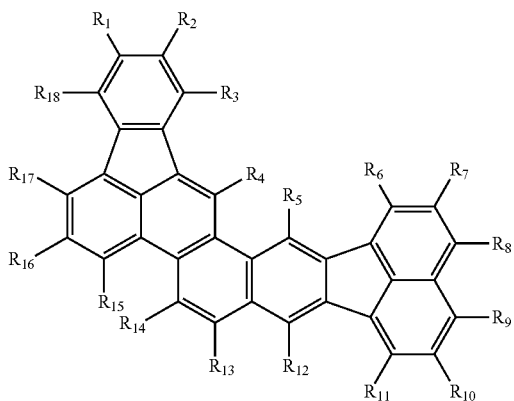

(1)

wherein $R_1$ to $R_{18}$ independently denote a hydrogen atom, a halogen atom, a substituted or unsubstituted alkyl group, a substituted or unsubstituted alkoxy group, a substituted or unsubstituted amino group, a substituted or unsubstituted aryl group, or a substituted or unsubstituted heterocyclic group.

2. The organic compound according to claim 1, wherein $R_1$ to $R_{18}$ independently denote a hydrogen atom, a substituted or unsubstituted alkyl group, or a substituted or unsubstituted aryl group.

3. The organic compound according to claim 2, wherein $R_1$, $R_2$, $R_8$, $R_9$, $R_{12}$, $R_{13}$, and $R_{15}$ independently denote a hydrogen atom or a substituted or unsubstituted aryl group.

4. The organic compound according to claim 2, wherein $R_1$, $R_2$, $R_8$, and $R_9$ independently denote a hydrogen atom or a substituted or unsubstituted aryl group.

5. The organic compound according to claim 2, wherein $R_{12}$, $R_{13}$, and $R_{15}$ independently denote a hydrogen atom or a substituted or unsubstituted aryl group.

6. An organic light-emitting device comprising:
   a pair of electrodes; and
   an organic compound layer disposed between the pair of electrodes, wherein the organic compound layer contains an organic compound according to claim 1.

7. The organic light-emitting device according to claim 6, wherein the organic compound layer is a light-emitting layer.

8. An image display apparatus comprising:
   an organic light-emitting device according to claim 6; and
   a switching device connected to the organic light-emitting device.

* * * * *